(12) United States Patent
Sukumar et al.

(10) Patent No.: US 10,316,361 B2
(45) Date of Patent: Jun. 11, 2019

(54) GENOME-WIDE METHYLATION ANALYSIS AND USE TO IDENTIFY GENES SPECIFIC TO BREAST CANCER HORMONE RECEPTOR STATUS AND RISK OF RECURRENCE

(75) Inventors: Saraswati V. Sukumar, Columbia, MD (US); Christopher Benedict Umbricht, Towson, MD (US); Antonio C. Wolff, Baltimore, MD (US); Mary Jo Steele Fackler, Hunt Valley, MD (US); Zhe Zhang, Columbia, MD (US); Leslie M. Cope, Baltimore, MD (US); Kala Visvanathan, Baltimore, MD (US); Peng Huang, Owings Mills, MD (US)

(73) Assignee: THE JOHN HOPKINS UNIVERSITY, Baltimore, MD (US)

( * ) Notice: Subject to any disclaimer, the term of this patent is extended or adjusted under 35 U.S.C. 154(b) by 164 days.

(21) Appl. No.: 14/232,981

(22) PCT Filed: Jul. 16, 2012

(86) PCT No.: PCT/US2012/046868
§ 371 (c)(1),
(2), (4) Date: Apr. 4, 2014

(87) PCT Pub. No.: WO2013/012781
PCT Pub. Date: Jan. 24, 2013

(65) Prior Publication Data
US 2014/0221242 A1 Aug. 7, 2014

Related U.S. Application Data

(60) Provisional application No. 61/508,381, filed on Jul. 15, 2011.

(51) Int. Cl.
*C12P 19/34* (2006.01)
*C12Q 1/68* (2018.01)
*C12Q 1/6874* (2018.01)
*C12Q 1/6886* (2018.01)

(52) U.S. Cl.
CPC ......... *C12Q 1/6874* (2013.01); *C12Q 1/6886* (2013.01); *C12Q 2600/112* (2013.01); *C12Q 2600/118* (2013.01); *C12Q 2600/154* (2013.01)

(58) Field of Classification Search
CPC ............ C12Q 1/6886; C12Q 2600/118; C12Q 2600/154; C12Q 1/6874; C12Q 2600/112; C12Q 2523/125; C12Q 2545/114
See application file for complete search history.

(56) References Cited

U.S. PATENT DOCUMENTS

| 8,062,849 B2 | 11/2011 | Sukumar et al. |
| 2005/0239101 A1 | 10/2005 | Sukumar et al. |
| 2007/0298506 A1 | 12/2007 | Ordway et al. |
| 2012/0202202 A1 | 8/2012 | Wang et al. |

FOREIGN PATENT DOCUMENTS

| EP | 2233590 A1 | 9/2010 |
| WO | 2005059172 A2 | 6/2005 |

OTHER PUBLICATIONS

Li L. et al. Human Molecular Genetics, 2010, vol. 19, No. 21, pp. 4273-4277.*
Li et al. "Abstract #5189: Genome wide methylation profiles are different by the estrogen and progesterone receptor status of breast tumors" Cancer Res May 1, 2009 69; 5189.*
Van der Auwera I. et al. PLoS ONE (Sep. 2010) vol. 5, Issue 9, e12616, 10 printed pages.*
Lenz G. et al. Ann Hematol (2004) 83: 628-633.*
Costello J.F. et al. The journal of Biological Chemisrty. vol. 269, No. 25, Isaue of Jun. 24, pp. 17228-17237, (1994).*
Bibkova M. et al. Future Medicine—Epigenomics (2009) 1(1) 177-200.*
Illingworth, R. et al. (2008) A novel CpG island set identifies tissue-specific methylation at developmental gene loci. PLoS Biol 6(1): e22. pp. 0037-0051. (Year: 2008).*
Fackler, M., et al., "Genome-wide methylation analysis identifies genes specific to breast cancer hormone receptor status and risk of recurrence", Cancer Res., Aug. 8, 2011, vol. 71, No. 19, pp. 6195-6207.
Pan et al (2010) Long form collapsin response mediator protein-1 (LCRMP-1) expression is associated with clinical outcome and lymph node metastasis in non-small cell lung cancer patients. Lung Cancer 67:93-100.
Zou et al (2005) Frequent methylation of eyes absent 4 gene in Barrett's esophagus and esophageal adenocarcinoma. Cancer Epidemiol Biomarkers Prev 14:830-834.
Oster et al (2011) Identification and validation of highly frequent CpG island hypermethylation in colorectal adenomas and carcinomas. Int J Cancer 15:129.
Peng et al (2009) DNA hypermethylation regulates the expression of members of the Mu-class glutathione S-transferases and glutathione peroxidases in Barrett's adenocarcinoma. Gut 58:5-15.
Starkova et al (2010) HOX gene expression in phenotypic and genotypic subgroups and low HOXA gene expression as an adverse prognostic factor in pediatric ALL. Pediatr Blood Cancer 55:1072-1082.

(Continued)

*Primary Examiner* — Stephen T Kapushoc
(74) *Attorney, Agent, or Firm* — John Hopkins Technology Ventures

(57) ABSTRACT

To better understand the biology of hormone receptor-positive and negative breast cancer and to identify methylated gene markers of disease progression, a genome-wide methylation array analysis was performed on 103 primary invasive breast cancers and 21 normal breast samples using the Illumina Infinium HumanMethylation27 array that queried 27,578 CpG loci. Forty CpG loci showed differential methylation specific to either ER-positive or ER-negative tumors. Each of the 40 ER-subtype-specific loci was validated in silico using an independent, publicly available methylome dataset from The Cancer Genome Atlas (TCGA). In addition, 100 methylated CpG loci were identified that were significantly associated with disease progression. Arrays containing the ER-subtype-specific loci and their use in methods of diagnosis and treatment of breast cancer are provided.

10 Claims, 11 Drawing Sheets
Specification includes a Sequence Listing.

(56) References Cited

OTHER PUBLICATIONS

Tommasi et al (2009) Methylation of homeobox genes is a frequent and early epigenetic event in breast cancer. Breast Cancer Res 11:R14.
Rodriguez et al (2008) Epigenetic repression of the estrogen-regulated Homeobox B13 gene in breast cancer. Carcinogenesis 29:1459-1465.
Ghoshal et al (2010) HOXB13, a target of DNMT3B, is methylated at an upstream CpG island, and functions as a tumor suppressor in primary colorectal tumors. PLoS One 5:e10338.
Ma et al (2008) A five-gene molecular grade index and HOXB13:IL17BR are complementary prognostic factors in early stage breast cancer. Clin Cancer Res 14:2601-2608.
Sgroi (2009) The HOXB13:IL17BR gene-expression ratio: a biomarker providing information above and beyond tumor grade. Biomark Med 3:99-102.
Kim et al (2011) Epigenomic analysis of aberrantly methylated genes in colorectal cancer identifies genes commonly affected by epigenetic alterations. Ann Surg Oncol 18:2338-2347.
Jin et al (2009) A multicenter, double-blinded validation study of methylation biomarkers for progression prediction in Barrett's esophagus. Cancer Res 69:4112-4115.
Tony et al (2010) Genome-wide DNA methylation profiling of chronic lymphocytic leukemia allows identification of epigenetically repressed molecular pathways with clinical impact. Epigenetics 5:499-508.
Sato et al (2008) CpG island methylation profile of pancreatic intraepithelial neoplasia. Mod Pathol 21:238-244.
Herbst et al (2011) Methylation of NEUROG1 in serum is a sensitive marker for the detection of early colorectal cancer. Am J Gastroenterol 106:1110-1118.
Lai et al (2008) Identification of novel DNA methylation markers in cervical cancer. Int J Cancer 123:161-167.
Rahmatpanah et al (2006) Differential DNA methylation patterns of small B-cell lymphoma subclasses with different clinical behavior. Leukemia 20:1855-1862.
Katoh et al (2009) Integrative genomic analyses of ZEB2: Transcriptional regulation of ZEB2 based on SMADs, ETS1, HIF1alpha, POU/OCT, and NF-kappaB. Int J Oncol 34:1737-1742.
Fevre-Montange et al (2006) Microarray analysis reveals differential gene expression patterns in tumors of the pineal region. J Neuropathol Exp Neurol 65:675-684.
Matsubara et al (1994) Mapping and characterization of a retinoic acid-responsive enhancer of midkine, a novel heparin-binding growth/differentiation factor with neurotrophic activity. J Biochem 115:1088-1096.
Dalgin et al (2008) Identification of novel epigenetic markers for clear cell renal cell carcinoma. J Urol 180:1126-1130.
Aruga et al (2003) Human SLITRK family genes: genomic organization and expression profiling in normal brain and brain tumor tissue. Gene 315:87-94.
Fang et al (2009) Expression of Cyclophilin B is Associated with Malignant Progression and Regulation of Genes Implicated in the Pathogenesis of Breast Cancer. Am J PAthol 174:297-308.
Singer et al (2009) Coordinated expression of stathmin family members by far upstream sequence element-binding protein-1 increases motility in non-small cell lung cancer. Cancer Res 69:2234-2243.
Van der Auwera et al (2010). Quantitative methylation profiling in tumor and matched morphologically normal tissues from breast cancer patients. BMC Cancer 10:97.
Van der Auwera et al (2010) Array-based DNA methylation profiling for breast cancer subtype discrimination. PLOS One 5:e12616.
Harris et al (2007) American Society of Clinical Oncology 2007 update of recommendations for the use of tumor markers in breast cancer. J Clin Oncol 25:5287-5312.
Hammond et al (2010) American Society of Clinical Oncology/College of American Pathologists guideline recommendations for immunohistochemical testing of estrogen and progesterone receptors in breast cancer. J Clin Oncol 28:2784-2795.

Wolff et al (2007) American Society of Clinical Oncology/College of American Pathologists guideline recommendations for human epidermal growth factor receptor 2 testing in breast cancer. J Clin Oncol 25:118-145.
Fisher et al (2001) Findings from recent National Surgical Adjuvant Breast and Bowel Project adjuvant studies in stage I breast cancer. J Natl Cancer Inst Monogr 30:62-66.
Marchionni et al (2008) Systematic Review: Gene Expression Profiling Assays in Early-Stage Breast Cancer. Ann Intern Med 148:358-369.
Paik et al (2004) A Multigene Assay to Predict Recurrence of Tamoxifen-Treated, Node-Negative Breast Cancer. N Engl J Med 351:2817-2826.
Buyse et al (2006) Validation and clinical utility of a 70-gene prognostic signature for women with node-negative breast cancer. J Natl Cancer Inst 98:1183-1192.
Simon (2006) Development and evaluation of therapeutically relevant predictive classifiers using gene expression profiling. J Natl Cancer Inst 98:1169-1171.
Paik et al (2006) Gene expression and benefit of chemotherapy in women with node-negative, estrogen receptor-positive breast cancer. J Clin Oncol 24:3726-3734.
Fisher et al (2001) Prognosis and treatment of patients with breast tumors of one centimeter or less and negative axillary lymph nodes. J Natl Cancer Inst 93:112-120.
Sharma et al (2010) Epigenetics in cancer. Carcinogenesis 31:27-36.
Fackler et al (2006) Quantitative multiplex methylation-specific PCR analysis doubles detection of tumor cells in breast ductal fluid. Clin Cancer Res 12:3306-3310.
Hill et al (2011) Genome-wide DNA methylation profiling of CpG islands in breast cancer identifies novel genes associated with tumorigenicity. Cancer Res 71:2988-2999.
Locke et al (2007) Gene promoter hypermethylation in ductal lavage fluid from healthy BRCA gene mutation carriers and mutation-negative controls. Breast Cancer Res 9:R20.
Fackler et al (2009) Hypermethylated genes as biomarkers of cancer in women with pathologic nipple discharge. Clin Cancer Res 15:3802-3811.
Fackler et al (2003) DNA methylation of RASSF1A, HIN-1, RAR-beta, Cyclin D2 and Twist in in situ and invasive lobular breast carcinoma. Int J Cancer 107:970-975.
Lee et al (2008) Quantitative promoter hypermethylation profiles of ductal carcinoma in situ in North American and Korean women: Potential applications for diagnosis. Cancer Biol Ther 7:1398-1406.
Lehmann et al (2002) Quantitative assessment of promoter hypermethylation during breast cancer development. Am J Pathol 160:605-612.
Umbricht et al (2001) Hypermethylation of 14-3-3 sigma (stratifin) is an early event in breast cancer. Oncogene 20:3348-3353.
Li et al (2010) Estrogen and progesterone receptor status affect genome-wide DNA methylation profile in breast cancer. Hum Mol Genet 19:4273-4277.
Holm et al (2010) Molecular subtypes of breast cancer are associated with characteristic DNA methylation patterns. Breast Cancer Res 12:R36.
Fackler et al (2004) Quantitative multiplex methylation-specific PCR assay for the detection of promoter hypermethylation in multiple genes in breast cancer. Cancer Res 64:4442-4452.
Swift-Scanlon et al (2006) Two-color quantitative multiplex methylation-specific PCR. Biotechniques 40:210-219.
Kamalakaran et al (2011) DNA methylation patterns in luminal breast cancers differ from non-luminal subtypes and can identify relapse risk independent of other clinical variables. Molecular Oncology 5:77-92.
Albain et al (2009) Prediction of adjuvant chemotherapy benefit in endocrine responsive, early breast cancer using multigene assays. Breast 18 Suppl 3:S141-145.
Kim et al (2010) Gene-expression-based prognostic assays for breast cancer. Nature reviews Clinical Oncology 7:340-347.
Sjoblom et al (2006) The Consensus Coding Sequences of Human Breast and Colorectal Cancers. Science 314:268-274.

(56) References Cited

OTHER PUBLICATIONS

Leary et al (2008) Integrated analysis of homozygous deletions, focal amplifications, and sequence alterations in breast and colorectal cancers. Proc Natl Acad Sci U S A 105:16224-16229.

Wood et al (2007) The genomic landscapes of human breast and colorectal cancers. Science 318:1108-1113.

Shah et al (2010) The Hox genes and their roles in oncogenesis. Nature reviews Cancer 10:361-371.

Choschzick et al (2010) Overexpression of cell division cycle 7 homolog is associated with gene amplification frequency in breast cancer. Hum Pathol 41:358-365.

Charafe-Jauffret et al (2006) Gene expression profiling of breast cell lines identifies potential new basal markers. Oncogene 25:2273-2284.

Patel et al (2011) Control of EVI-1 oncogene expression in metastatic breast cancer cells through microRNA miR-22. Oncogene 30:1290-1301.

Dejeux et al (2010) DNA methylation profiling in doxorubicin treated primary locally advanced breast tumours identifies novel genes associated with survival and treatment response. Mol Cancer 9:68.

Neve et al (2006) A collection of breast cancer cell lines for the study of functionally distinct cancer subtypes. Cancer Cell 10:515-527.

Lau et al (2006) RUNX3 is frequently inactivated by dual mechanisms of protein mislocalization and promoter hypermethylation in breast cancer. Cancer Res 66:6512-6520.

Fiegl et al (2006) Breast Cancer DNA methylation profiles in cancer cells and tumor stroma: association with HER-2/neu status in primary breast cancer. Cancer Res 66:29-33.

Carlson et al (2009) Breast cancer. Clinical practice guidelines in oncology. J Natl Compr Canc Netw 7:122-192.

Choi et al (2010) LYN is a mediator of epithelial-mesenchymal transition and a target of dasatinib in breast cancer. Cancer Res 70:2296-2306.

Fu et al (2010) Frequent epigenetic inactivation of the receptor tyrosine kinase EphA5 by promoter methylation in human breast cancer. Hum Pathol 41:48-58.

Fang et al (2011) Breast cancer methylomes establish an epigenomic foundation for metastasis. Sci Transl Med 3:75ra25.

Smyth (2004) Linear models and empirical bayes methods for assessing differential expression in microarray experiments. Stat Appl Genet Mol Biol 3:1-25.

Dan et al (2003) Identification of candidate predictive markers of anticancer drug sensitivity using a panel of human cancer cell lines. Cancer Sci 94:1074-1082.

Lefrancois-Martinez et al (2004) Decreased expression of cyclic adenosine monophosphate-regulated aldose reductase (AKR1B1) is associated with malignancy in human sporadic adrenocortical tumors. J Clin Endocrinol Metab 89:3010-3019.

Dietrich et al (2010) CDO1 promoter methylation is a biomarker for outcome prediction of anthracycline treated, estrogen receptor-positive, lymph node-positive breast cancer patients. BMC Cancer 10:247.

Morris et al (2010) Identification of candidate tumour suppressor genes frequently methylated in renal cell carcinoma. Oncogene 29:2104-2117.

Paulus et al (1993) Characterization of integrin receptors in normal and neoplastic human brain. Am J Pathol 143:154-163.

Vachani et al (2007) A 10-gene classifier for distinguishing head and neck squamous cell carcinoma and lung squamous cell carcinoma. Clin Cancer Res 13:2905-2915.

\* cited by examiner

FIGURE 8

| CpG locus | Gene symbol_ID | Methylation asso. with recurrence in ER subgroup | Methylation or Altered expression in: Breast cancer | Methylation or Altered expression in: Other cancers | Expression asso. with recurrence/drug sensitivity |
|---|---|---|---|---|---|
| 1 | AKR1B1_cg13801416 | ER-pos, ER-neg | (5) | (6) | (5, 6) |
| 2 | AKR1B1_cg18416881 | ER-pos, ER-neg | (5) | (6) | (5, 6) |
| 3 | ALX1_cg02409351 | ER-neg | NK | NK | NK |
| 4 | CDO1_cg12880658 | ER-neg | NK | (7) | (7) |
| 5 | COL14A1_cg23196831 | ER-neg | NK | (8, 9) | NK |
| 6 | COL6A2_cg21513553 | ER-pos | NK | (10) | NK |
| 7 | CRMP1_cg22680204 | ER-pos | NK | (11) | NK |
| 8 | EPHA5_18420965 | ER-neg, | (12) | NK | (8) |
| 9 | EYA4_cg01401376 | ER-neg, | NK | (13, 14) | NK |
| 10 | EYA4_cg01805282 | ER-neg | NK | (13, 14) | NK |
| 11 | FLRT2_cg17410236 | ER-neg | NK | NK | NK |
| 12 | GPX7_cg16557944 | ER-pos | NK | (15) | (15) |
| 13 | GPX7_cg22129364 | ER-neg, | NK | (15) | (15) |
| 14 | HOXA13_cg10883303 | ER-pos | NK | NK | (16) |
| 15 | HOXB13_cg21842478 | ER-neg | (17, 18) | (19) | (20, 21) |
| 16 | HOXB13_cg15786837 | ER-neg | (17, 18) | (19) | (20, 21) |
| 17 | KCNB2_cg20890210 | ER-neg, | NK | NK | NK |
| 18 | LAMA1_cg07846220 | ER-neg, | NK | (22) | NK |
| 19 | LHX1_cg22660578 | ER-neg, | NK | (23, 24) | (23) |
| 20 | LHX2_cg07109287 | ER-neg, | (23) | (24, 25) | (24) |
| 21 | NEUROG1_cg04897683 | ER-neg, | NK | (26) | NK |
| 22 | NKX6-2_cg09260089 | ER-pos | NK | (27, 28) | (27) |
| 23 | NRP2_cgcg22367989 | ER-pos | NK | (28) | NK |
| 24 | POU3F2_cg14823162 | ER-neg | NK | (29, 30) | NK |
| 25 | POU4F2_cg24199834 | ER-neg | NK | NK | NK |
| 26 | POU4F2_cg13262687 | ER-neg | NK | NK | NK |
| 27 | REM1_cg26299767 | ER-pos | NK | (31) | NK |
| 28 | SCNN1B_cg23113963 | ER-pos | NK | (32) | NK |
| 29 | SLITRK3_cg13619915 | ER-neg | NK | (33) | NK |
| 30 | STMN3_cg08291098 | ER-neg | NK | (34, 35) | NK |
| 31 | TMEFF2_cg18221862 | ER-neg | NK | (23, 36) | (23, 36) |
| 32 | TMEM179_cg03734874 | ER-pos, | NK | NK | NK |

Supplemental Table 4C: Novel and known genes/CpG loci predictive of recurrence in breast cancer NK= not known, unidentified based on PubMed searches

FIGURE 9

| ER Subtype-Specific Biomarkers (40 CpG Loci; derived from 200 ER loci set) | | |
|---|---|---|
| TargetID | SYMBOL | PRODUCT |
| ER-Positive Biomarkers (27 CpG Loci) | | |
| cg09068528 | ACADL | acyl-Coenzyme A dehydrogenase; long chain precursor |
| cg00116234 | ADAMTSL1 | ADAMTS-like 1 isoform 2 |
| cg00079563 | ARFGAP3 | ADP-ribosylation factor GTPase activating protein 3 |
| cg07845566 | B3GAT1 | beta-1;3-glucuronyltransferase 1 |
| cg08690031 | CDCA7 | cell division cycle associated protein 7 isoform 1 |
| cg14998713 | ETS1 | v-ets erythroblastosis virus E26 oncogene homolog 1 |
| cg14228238 | EVI1 | ecotropic viral integration site 1 |
| cg12998491 | FAM78A | hypothetical protein LOC286336 |
| cg00679738 | FAM89A | hypothetical protein LOC375061 |
| cg01657408 | FLJ31951 (RNF145) | hypothetical protein LOC153830 |
| cg18108623 | FLJ34922 (SLFN11) | hypothetical protein FLJ34922 |
| cg26420196 | GAS6 | growth arrest-specific 6 |
| cg01561916 | HAAO | 3-hydroxyanthranilate 3;4-dioxygenase |
| cg01868782 | HEY2 | hairy/enhancer-of-split related with YRPW motif 2 |
| cg12370791 | HOXB9 | homeo box B9 |
| cg14188232 | ITGA11 | integrin; alpha 11 precursor |
| cg10539712 | LYN | v-yes-1 Yamaguchi sarcoma viral related oncogene homolog |
| cg02755525 | NETO2 | neuropilin- and tolloid-like protein 2 precursor |
| cg14019317 | PROX1 | prospero-related homeobox 1 |
| cg25336579 | PSAT1 | phosphoserine aminotransferase isoform 2 |
| cg15774283 | PTGS2 | prostaglandin-endoperoxide synthase 2 precursor |
| cg12717594 | RECK | RECK protein precursor |
| cg06377278 | RUNX3 | runt-related transcription factor 3 isoform 2 |
| cg15239123 | SMOC1 | secreted modular calcium-binding protein 1 |
| cg00893242 | SND1 | staphylococcal nuclease domain containing 1 |
| cg01186777 | TNFSF9 | tumor necrosis factor (ligand) superfamily; member 9 |
| cg12874092 | VIM | vimentin |

FIGURE 10

| ER-Negative Biomarkers (13 CpG Loci) | | |
|---|---|---|
| cg08090772 | ADHFE1 | alcohol dehydrogenase; iron containing; 1 |
| cg27650175 | DAB2IP | DAB2 interacting protein isoform 1 |
| cg14063008 | DAB2IP | DAB2 interacting protein isoform 1 |
| cg07981910 | DAB2IP | DAB2 interacting protein isoform 2 |
| cg05684891 | DAB2IP | DAB2 interacting protein isoform 2 |
| cg00720137 | DYNLRB2 | dynein; cytoplasmic; light polypeptide 2B |
| cg14874121 | HSD17B4 | estradiol 17 beta-dehydrogenase 4 |
| cg07433344 | HSD17B8 | estradiol 17 beta-dehydrogenase 8 |
| cg16541031 | IRF7 | interferon regulatory factor 7 isoform a |
| cg23178308 | PDXK | Pyridoxal (pyridoxine, vitamine B6) kinase |
| cg01980637 | PER1 | period 1 |
| cg17599586 | PISD | phosphatidylserine decarboxylase |
| cg08108311 | WNK4 | WNK lysine deficient protein kinase 4 |
| Abbreviations: TSS (transcriptional start site), na (not available), β-value: range 0-1 (low to high, respectively; approximately correlates with % methylation). | | |

GENOME-WIDE METHYLATION ANALYSIS AND USE TO IDENTIFY GENES SPECIFIC TO BREAST CANCER HORMONE RECEPTOR STATUS AND RISK OF RECURRENCE

CROSS-REFERENCE TO RELATED APPLICATIONS

This application is a 35 U.S.C. § 371 U.S. national entry of International Application PCT/US2012/46868, having an international filing date of Jul. 16, 2012, which claims the benefit of U.S. Provisional Application No. 61/508,381, filed Jul. 15, 2011, the content of each of the aforementioned applications is herein incorporated by reference in its entirety.

STATEMENT OF GOVERNMENTAL INTEREST

This invention was made with U.S. government support under grant no. CA088843. The U.S. government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jul. 16, 2012, is named P11625-02_ST25.txt and is 1,745 bytes in size.

BACKGROUND OF THE INVENTION

Approximately 200,000 women are diagnosed each year in the U.S. with breast cancer, and nearly 50,000 die of their metastatic disease. Significant improvement made in both early detection and local/systemic therapy in the last few decades has significantly improved patient outcomes, especially survival. Breast cancers are characterized by their estrogen and progesterone receptor status (hereon termed ER), and it is established that ER expression (ER+) identifies a tumor phenotype with improved near/mid-term prognosis and likely benefit from adjuvant endocrine therapy when compared to ER-negative (ER−) tumors. Yet, little is known about the genomic features within each ER subtype of breast cancer that could explain why some patients with the same ER status have a good outcome while others do poorly regardless of treatment.

Current decision algorithms based on standard clinico-pathologic factors stratify ER− disease as having a high-risk for recurrence. Although patients are now routinely offered adjuvant chemotherapy, most patients with node-negative, ER− disease remain disease-free after local therapy alone, including approximately 80% of ER− patients with tumors ≤1 cm and up to 60% of all with stage 1 disease. Consequently, there are patients with ER− disease that might do well without adjuvant chemotherapy and could avoid its potential toxicities, while others with a high residual risk despite it might be offered trials of novel therapies. Unfortunately, existing markers routinely used in clinical practice are of limited or no use in ER− patients. For example, commonly used gene expression tests by RT-PCR have no clear prognostic/predictive utility in ER− disease and microarray assays developed so far appear to identify essentially all such patients as high risk, while other markers are still in development. Consequently, there is a critical need to develop better prognostic factors to improve assessment of residual risk and better predictive markers to optimize patient selection for standard and investigational systemic therapies.

Methylated genes are particularly robust as biomarkers. In past studies, the present inventors developed a cancer detection panel using a quantitative cumulative methylation assay known as Quantitative Multiplex-Methylation Specific PCR (QM-MSP) (see, U.S. Pat. No. 8,062,849) wherein the methylation status of multiple genes could be determined individually and cumulatively from picograms of input DNA, such as is retrieved from ductal lavage or ductoscopy and pathologic nipple discharge fluid. It has also been found that methylated genes are frequently detected in the pre-invasive stage of DCIS. Further, histopathologically normal ducts in the vicinity of tumor tissue display detectable hypermethylation of genes that are present in the adjacent DCIS or invasive cancer, while normal ducts present farther away do not. However, using the candidate marker approach it has been difficult to identify markers informative of the biology specifically of ER-positive or negative breast cancer or those that predict response to therapy, disease progression and survival. Therefore, there still exists a need for a genome-wide discovery platform would identify gene loci in tumors that better predict clinical outcomes.

SUMMARY OF THE INVENTION

As the first step towards studies with clinical trial samples, the inventors performed methylation array analyses on a discovery set of 103 primary invasive tumors and 21 normal samples. It was found that distinctly different gene CpG loci typify the methylome of ER+ and ER− breast cancers. Forty target DNA gene loci were identified that stratified tumors according to ER-status. A putative "prognostic signature" of 100 target DNA gene CpG loci were also identified that are individually and collectively associated with outcome in patients with breast cancer. This present invention demonstrates that CpG locus methylation levels reveals important biological differences in the epigenome between breast cancer subtypes and provide ancillary clinical diagnostic, prognostic, and predictive tools.

In an embodiment, the present invention provides an array of oligonucleotide probes for identifying methylated target DNA genes in a sample, comprising one or more oligonucleotide probes that each selectively bind methylated loci in a target DNA gene and a platform; wherein the probes are immobilized on the platform; and wherein at least one or more probes selectively bind methylated target DNA genes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, TNFSF9, ADHFE1, DYN-LRB2, HSD17B8, PDXK, PISD and WNK4.

In another embodiment, the present invention provides an array of oligonucleotide probes for identifying methylated target DNA genes in a sample, comprising one or more oligonucleotide probes that each selectively bind methylated loci in a target DNA gene, and a platform; wherein the probes are immobilized on the platform; and wherein at least two or more probes selectively bind methylated target DNA genes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, TNFSF9, EVI1, ETS1, IRF7, LYN, PTGS2 (COX2), RUNX3, VIM, PDXK, ADHFE1, DYNLRB2, HSD17B8, PDXK, PISD, WNK4, DAB2IP, HSD17B4, and PER1.

In a further embodiment, the present invention provides a biochip comprising a solid substrate further comprising at least two oligonucleotide probes that each selectively bind methylated loci in a target DNA genes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, TNFSF9, ADHFE1, DYNLRB2, HSD17B8, PDXK, PISD and WNK4.

In yet another embodiment, the present invention provides a method for determining the methylation status of one or more target genes in a breast tissue sample from a subject comprising: a) obtaining a biological sample of comprising DNA from the breast tissue of the subject; b) extracting DNA from the sample of a); c) contacting the DNA from b) with the above arrays or biochip; d) performing an analysis using the array or biochip of c) to determine the methylation of at least one or more target DNA genes obtained from the sample; and e) comparing the methylation of at least one or more target DNA genes obtained from the sample tissue with the methylation of at least one target DNA gene obtained from a control sample, wherein a detectable increase in the methylation of at least one or more target DNA genes obtained from the sample compared to control wherein when the amount of methylation on at least one or more DNA target genes is greater than the amount of methylation in the control sample, the target DNA gene is considered to be methylated.

In still another embodiment, the present invention provides a method for diagnosing the presence of an ER+ or ER− breast cancer in a subject comprising: a) obtaining a biological sample comprising DNA from the breast tissue of the subject; b) extracting DNA from the sample of a); c) contacting the DNA from (b) with the above arrays or biochip; d) performing an analysis using the array or biochip of c) to determine the methylation of at least one or more target DNA genes obtained from the sample; e) detecting the amount of methylation on at least one or more target DNA genes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, and TNFSF9, or, f) detecting the amount of methylation on at least one or more target DNA genes selected from the group consisting of ADHFE1, DYNLRB2, HSD17B8, PDXK, PISD, and WNK4; g) comparing the amount of methylation on at least one or more target DNA genes in the sample from the subject to the amount of methylation in a control sample; wherein when methylation is detected on one or more target DNA genes from e) the subject is diagnosed as having ER+ breast cancer, and wherein when methylation is detected on one or more target DNA genes from f) the subject is diagnosed as having ER− breast cancer.

In an embodiment, the present invention provides a method for diagnosing the presence of an ER+ or ER− breast cancer in a subject comprising: a) obtaining a biological sample of comprising DNA from the breast tissue of the subject; b) extracting DNA from the sample of a); c) contacting the DNA from (b) with the above arrays or biochip; d) performing an analysis using the array or biochip of c) to determine the methylation of at least two or more target DNA genes obtained from the sample; e) detecting the amount of methylation on at least two or more DNA target probes selected from the group consisting of detecting the amount of methylation on at least two or more DNA target probes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO, PROX1, PSAT1, RECK, SMOC1, SND1, TNFSF9, EVI1, ETS1, IRF7, LYN, PTGS2 (COX2), RUNX3, and VIM, or, f) detecting the amount of methylation on at least two or more DNA target probes selected from the group consisting of ADHFE1, DYNLRB2, HSD17B8, PDXK, PISD, WNK4, DAB2IP, HSD17B4, and PER1; g) comparing the amount of methylation on at least two or more DNA target sites in the sample from the subject to the amount of methylation in a control sample; wherein when methylation is detected on two or more target DNA probes from e) the subject is diagnosed as having ER+ breast cancer, and wherein when methylation is detected on two or more target DNA probes from f) the subject is diagnosed as having ER− breast cancer.

In another embodiment, the present invention provides a method for predicting poor treatment outcome in a subject having breast cancer comprising: a) obtaining a biological sample of comprising DNA from the breast tumor tissue of the subject; b) extracting DNA from the sample of a); c) contacting the DNA from (b) with the above arrays or biochip; d) performing an analysis using the array or biochip of c) to determine the methylation of at least one or more target DNA genes obtained from the sample; e) detecting the amount of methylation on at least one or more DNA target genes selected from the group consisting of TMEM179, CRMP1 and SCNN1B in ER+ breast tumor tissue, or f) detecting the amount of methylation on at least one or more target DNA genes selected from the group consisting of ALX1, CDO1, COL14A1, EPHA5, EYA4, FLRT2, GPX7, KCNB2, *LAMA*1, LHX1, LHX2, NEUROG1, POU3F2, TMEFF2 and STMN3 in ER− breast tumor tissue, or g) detecting the amount of methylation on at least one or more DNA target genes selected from the group consisting of AKR1B1, COL6A2, EYA4, GPX7, HOXA13, HOXB13, NKX6-2, NRP2, POU4F2, REM1, and SLITRK3 in either or both ER+ or ER− breast tumor tissue; h) comparing the amount of methylation on at least one or more target DNA genes in the sample from the subject to the amount of methylation in a control sample; wherein when methylation is detected on one or more target DNA genes from e) or f) and/or g) the subject is diagnosed as having a high likelihood of recurrent breast cancer.

In an embodiment, the present invention provides a method for determining the methylation status of one or more target genes in a breast tissue sample from a subject comprising: a) obtaining a biological sample of comprising DNA from the breast tissue of the subject; b) extracting DNA from the sample of a); c) performing QM-MSP analysis on DNA of b) to determine the methylation of at least one or more target DNA gene loci obtained from the sample; and d) comparing the methylation of at least one or more target DNA gene loci obtained from the sample tissue with the methylation of at least one target DNA gene obtained from a control sample, wherein a detectable increase in the methylation of at least one or more target DNA genes obtained from the sample compared to control wherein when the amount of methylation on at least one or more DNA target gene loci is greater than the amount of methylation in the control sample, the target DNA gene loci is considered to be methylated.

In still another embodiment, the present invention provides a method for diagnosing the presence of an ER+ or ER− breast cancer in a subject comprising: a) obtaining a biological sample comprising DNA from the breast tissue of the subject; b) extracting DNA from the sample of a); c) performing QM-MSP analysis on DNA of b), to determine the methylation of at least one or more target DNA genes obtained from the sample; c) detecting the amount of methylation on at least one or more DNA targets DNA genes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, and TNFSF9, or, d) detecting the amount of methylation on at least one or more target DNA genes selected from the group consisting of ADHFE1, DYNLRB2, HSD17B8, PDXK, PISD, and WNK4; e) comparing the amount of methylation on at least one or more target DNA genes in the sample from the subject to the amount of methylation in a control sample; wherein when methylation is detected on one or more target DNAs genes from c) the subject is diagnosed as having ER+ breast cancer, and wherein when methylation is detected on one or more target DNAs genes from d) the subject is diagnosed as having ER− breast cancer.

In still another embodiment, the present invention provides a method for diagnosing the presence of an ER+ or ER− breast cancer in a subject comprising: a) obtaining a biological sample of comprising DNA from the breast tissue of the subject; b) extracting DNA from the sample of a); c) performing QM-MSP analysis on DNA of b), to determine the methylation of at least two or more target DNA genes obtained from the sample; c) detecting the amount of methylation on at least two or more DNA targets selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO, PROX1, PSAT1, RECK, SMOC1, SND1, TNFSF9, EVIL ETS1, IRF7, LYN, PTGS2 (COX2), RUNX3, and VIM, or, c) detecting the amount of methylation on at least two or more DNA target probes selected from the group consisting of ADHFEL DYNLRB2, HSD17B8, PDXK, PISD, WNK4, DAB2IP, HSD17B4, and PER1; d) comparing the amount of methylation on at least two or more DNA target sites in the sample from the subject to the amount of methylation in a control sample; wherein when methylation is detected on two or more target DNA probes from b) the subject is diagnosed as having ER+ breast cancer, and wherein when methylation is detected on two or more target DNA probes from c) the subject is diagnosed as having ER− breast cancer.

In an embodiment, the present invention provides a method for predicting poor treatment outcome in a subject having breast cancer comprising: a) obtaining a biological sample comprising DNA from the breast tumor tissue of the subject; b) extracting DNA from the sample of a); c) performing QM-MSP analysis on DNA of b), to determine the methylation of at least one or more target DNA genes selected from the group consisting of TMEM179, CRMP1 and SCNN1B in ER+ breast tumor tissue, or e d) detecting the amount of methylation of at least one or more DNA target genes selected from the group consisting of ALX1, CDO1, COL14A1, EPHA5, EYA4, FLRT2, GPX7, KCNB2, LAMA1, LHX1, LHX2, NEUROG1, POU3F2, TMEFF2 and STMN3 in ER− breast tumor tissue, or e) detecting the amount of methylation of at least one or more DNA target genes selected from the group consisting of AKR1B1, COL6A2, EYA4, GPX7, HOXA13, HOXB13, NKX6-2, NRP2, POU4F2, REM1, and SLITRK3 in either or both ER+ or ER− breast tumor tissue; e) comparing the amount of methylation of at least one or more DNA target genes in the sample from the subject to the amount of methylation at least one or more DNA target genes in a control sample; wherein when methylation is detected on one or more target DNA genes from c) or d) and/or e) the subject is diagnosed as having a high likelihood of recurrent breast cancer.

In an embodiment, the present invention provides a method for determining the methylation status of a breast tissue sample from a subject comprising: a) obtaining a biological sample comprising DNA from the breast tissue of the subject; b) extracting DNA from the sample of a); c) performing methylation analysis on DNA of b) to determine the methylation of at least two or more target DNA genes on at least two or more target DNA genes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, TNFSF9, ADHFE1, DYNLRB2, HSD17B8, PDXK, PISD, WNK4, EVI1, ETS1, IRF7, LYN, PTGS2 (COX2), RUNX3, VIM, DAB2IP, HSD17B4, PER1, and PDXK; d) comparing the amount of methylation on at least two or more target DNA genes in the sample from the subject to the amount of methylation of two or more target DNA genes in a control sample, wherein when the amount of methylation of at least two or more target DNA genes in the sample from the subject is greater than the amount of methylation of at least two or more target DNA genes in the control sample, the target DNA genes are considered to be methylated.

In a further embodiment, the present invention provides a method for diagnosing the presence of a ER+ or ER− breast cancer in a subject comprising: a) obtaining a biological sample of comprising DNA from the breast tissue of the subject; b) extracting DNA from the sample of a); c) performing methylation analysis on DNA of b) to determine the methylation of at least two or more target DNA genes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO, PROX1, PSAT1, RECK, SMOC1, SND1, TNFSF9, EVIL ETS1, IRF7, LYN, PTGS2 (COX2), RUNX3, and VIM, or, c) detecting the amount of methylation on at least two or more DNA target probes selected from the group consisting of ADHFEL DYNLRB2, HSD17B8, PDXK, PISD, WNK4, DAB2IP, HSD17B4, and PER1; d) comparing the amount of methylation of at least two or more DNA target genes in the sample from the subject to the amount of methylation of at least two or more DNA target genes in a control sample; wherein when methylation is detected on two or more target DNA genes from b) the subject is diagnosed as having ER+ breast cancer, and wherein when methylation is detected on two or more target DNA genes from c) the subject is diagnosed as having ER− breast cancer.

In yet another embodiment, the present invention provides a method for diagnosing the presence of a ER+ or ER− breast cancer in a subject comprising: a) obtaining a biological sample ef comprising DNA from the breast tissue of the subject; b) extracting DNA from the sample of a); c) performing methylation analysis on DNA of b) to determine the methylation of at least one or more target DNA genes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, and TNFSF9, or, c) detecting the amount of methylation of at least one or more target DNA genes selected from the group consisting of ADHFE1, DYNLRB2, HSD17B8, PDXK, PISD, and WNK4; d) comparing the amount of methylation of at least one or more target DNA genes in the sample from the subject to the amount of methylation of at least one or more target DNA genes in a control sample; wherein when methylation is detected on one or more target DNA genes from c) the subject is diagnosed as having ER+ breast cancer, and wherein when methylation is detected on one or more target DNA genes from d) the subject is diagnosed as having ER− breast cancer.

In an embodiment, the present invention provides a method for predicting poor treatment outcome in a subject having breast cancer comprising: a) obtaining a biological sample comprising DNA from the breast tissue of the subject; b) extracting DNA from the sample of a); c) performing methylation analysis on DNA of b) to determine the methylation of at least one or more target DNA genes selected from the group consisting of TMEM179, CRMP1 and SCNN1B in ER+ breast tumor tissue, or c) detecting the amount of methylation of at least one or more target DNA genes selected from the group consisting of ALX1, CDO1, COL14A1, EPHA5, EYA4, FLRT2, GPX7, KCNB2, *LAMA*1, LHX1, LHX2, NEUROG1, POU3F2, TMEFF2 and STMN3 in ER− breast tumor tissue, or d) detecting the amount of methylation of at least one or more target DNA genes selected from the group consisting of AKR1B1, COL6A2, EYA4, GPX7, HOXA13, HOXB13, NKX6-2, NRP2, POU4F2, REM1, and SLITRK3 in both ER+ or ER− breast tumor tissue; e) comparing the amount of methylation of at least one or more target DNA genes in the sample from the subject to the amount of methylation of at least one or more target DNA genes in a control sample; wherein when methylation is detected on one or more target DNA genes from c) or d) and/or e) the subject is diagnosed as having a high likelihood of recurrent breast cancer.

BRIEF DESCRIPTION OF THE DRAWINGS

FIG. 8 is a table listing the novel and previously known genes/CpG loci predictive of recurrence in breast cancer.

FIG. 9 is a table of the ER+ methylation biomarkers associated with breast cancer.

FIG. 10 is a table of the ER− methylation biomarkers associated with breast cancer.

DETAILED DESCRIPTION OF THE INVENTION

Figure 1:
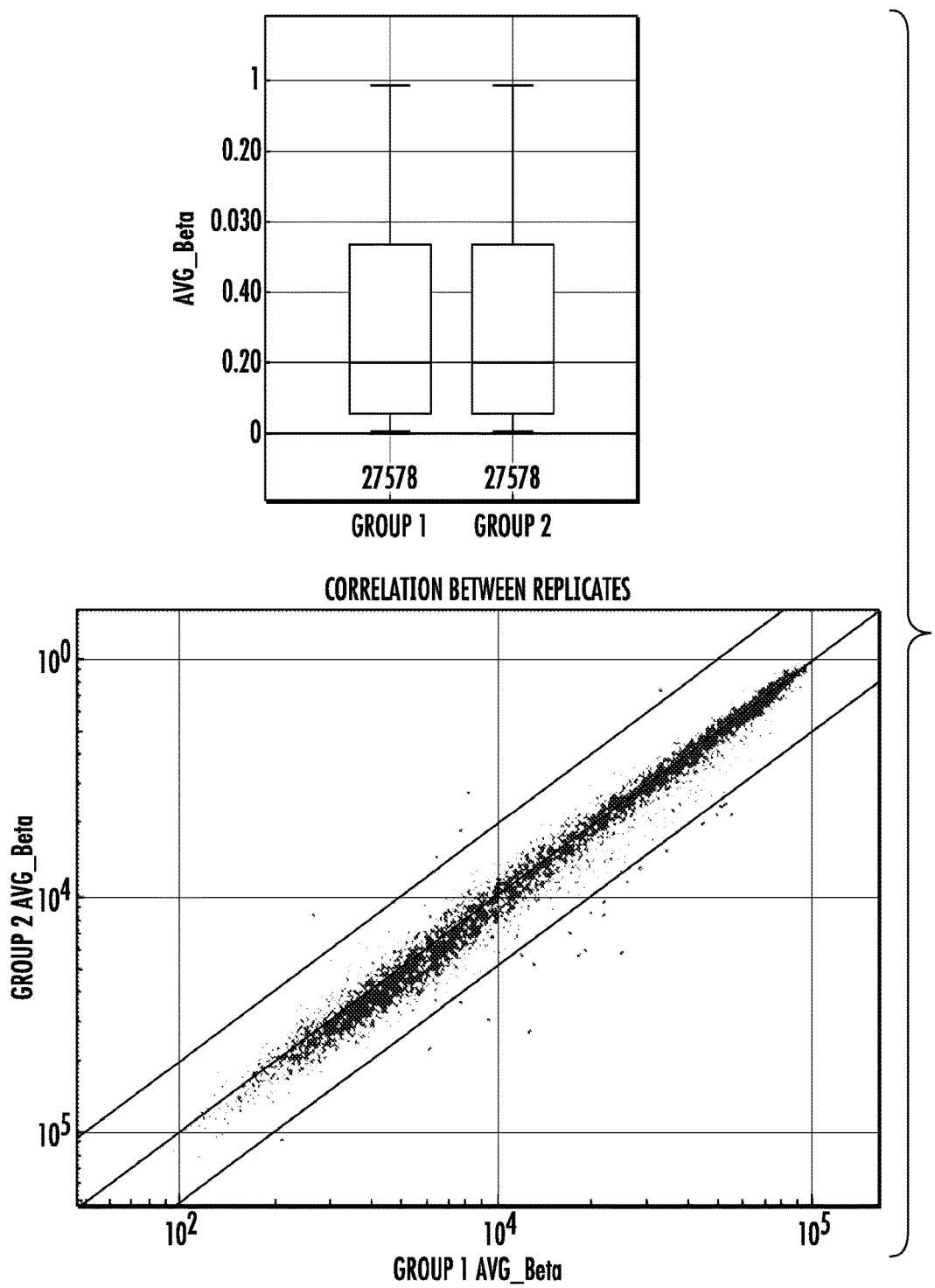
FIG. 1 DNA extraction and quality assurance were performed as described in Cancer Res. 2004; 64:4442-52 and Biotechniques. 2006; 40:210-9. A histogram of the two groups and a correlation plot of the two groups are shown.

The present invention provides the results of a genome wide array analysis of primary invasive breast cancers of 27,578 CpG loci. The inventors identified hypermethylated genes that specifically segregate with ER+ or ER− tumor subtypes, which were then validated in silico using the newly populated TCGA breast cancer database. The array analysis also identified 100 gene loci that were enriched for homeobox-containing genes and predicted recurrence in breast cancers. Many novel hypermethylated loci were identified.

In an embodiment, the present invention provides an array of oligonucleotide probes for identifying methylated target DNA genes in a sample, comprising oligonucleotide probes that each selectively bind methylated loci in a target DNA gene and a platform; wherein the are immobilized on the platform; and wherein at least one or more probes selectively bind methylated target DNA genes selected from the group consisting of ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, TNFSF9, ADHFE1, DYNLRB2, HSD17B8, PDXK, PISD and WNK4.

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind. In accordance with one or more embodiments, the term "probe" also means an oligonucleotide which is capable of specifically binding to a CpG locus which can be methylated. The probes of the present invention are used to determine the methylation status of at least one CpG dinucleotide sequence of at least one target DNA gene as described herein.

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

A probe is also provided comprising a nucleic acid described herein. Probes may be used for screening and diagnostic methods, as outlined below. The probes may be attached or immobilized to a solid substrate or apparatus, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

In accordance with one or more embodiments, the arrays of the present invention further comprise at least one randomly-generated oligonucleotide probe sequence used as a negative control; at least one oligonucleotide sequence derived from a housekeeping gene, used as a negative control for total DNA degradation; at least one randomly-generated sequence used as a positive control; and a series of dilutions of at least one positive control sequence used as saturation controls; wherein at least one positive control sequence is positioned on the array to indicate orientation of the array.

A biochip is also provided. The biochip is an apparatus which, in certain embodiments, comprises a solid substrate comprising an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. In an embodiment, two or more probes per target sequence are used. The probes may be capable of hybridizing to target sequences associated with a single disorder.

The probes may be attached to the biochip in a wide variety of ways, as will be appreciated by those in the art. The probes may either be synthesized first, with subsequent attachment to the biochip, or may be directly synthesized on the biochip.

In accordance with one or more embodiments, the biochips of the present invention are capable of hybridizing to a target sequence under stringent hybridization conditions and attached at spatially defined address on the substrate.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linkers. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

Exemplary biochips of the present invention include an organized assortment of oligonucleotide probes described above immobilized onto an appropriate platform. In accordance with another embodiment, the biochip of the present invention can also include one or more positive or negative controls. For example, oligonucleotides with randomized sequences can be used as positive controls, indicating orientation of the biochip based on where they are placed on the biochip, and providing controls for the detection time of the biochip when it is used for detecting methylated gene targets from a sample.

Embodiments of the biochip can be made in the following manner. The oligonucleotide probes to be included in the biochip are selected and obtained. The probes can be selected, for example, based on a particular subset target DNA genes of interest. The probes can be synthesized using methods and materials known to those skilled in the art, or they can be synthesized by and obtained from a commercial source, such as GeneScript USA (Piscataway, N.J.).

Each discrete probe is then attached to an appropriate platform in a discrete location, to provide an organized array of probes. Appropriate platforms include membranes and glass slides. Appropriate membranes include, for example, nylon membranes and nitrocellulose membranes. The probes are attached to the platform using methods and materials known to those skilled in the art. Briefly, the probes can be attached to the platform by synthesizing the probes directly on the platform, or probe-spotting using a contact or non-contact printing system. Probe-spotting can be accomplished using any of several commercially available systems, such as the GeneMachines™ OmniGrid (San Carlos, Calif.).

The biochips are scanned, for example, using an Epson Expression 1680 Scanner (Seiko Epson Corporation, Long Beach, Calif.) at a resolution of about 1500 dpi and 16-bit grayscale. The biochip images can be analyzed using Array-Pro Analyzer (Media Cybernetics, Inc., Silver Spring, Md.) software. Because the identity of the target DNA gene probes on the biochip are known, the sample can be identified as including particular target DNA genes when spots of hybridized target DNA genes-and-probes are visualized. Additionally, the density of the spots can be obtained and used to quantitate the identified target DNA genes in the sample.

The methylation state of a disease-associated target DNA gene provides information in a number of ways. For example, a differential methylation state of a cancer-associated gene target compared to a control may be used as a diagnostic that a patient suffers from breast cancer. Methylation states of a cancer-associated gene targets may also be used to monitor the treatment and disease state of a patient. Furthermore, Methylation states of a cancer-associated gene targets may allow the screening of drug candidates for altering a particular expression profile or suppressing an expression profile associated with cancer.

It will be understood by those of ordinary skill in the cancer treatment arts, that the methylation status of the target DNA genes of the present invention can be used to alter the standard treatments given to subjects diagnosed with breast cancer. For example, it is possible for a clinician to withhold drug all together (e.g., prognosis is good), such as when the tumor is identified as ER−, and doesn't have a recurrence marker, or, for a clinician to change to a different class of drug, combine drugs or increase dosage (e.g., prognosis is bad) such as when the tumor is identified as ER+, and may also have a recurrence marker. Thus, the information given by the arrays and methods described herein can be used to diagnose and to alter the treatment of subjects with breast cancer.

In an embodiment, the present invention provides a method for determining the methylation status of a breast tissue sample from a subject comprising: a) obtaining a biological sample comprising DNA from the breast tissue of the subject; b) extracting DNA from the sample of a); c) contacting the DNA from b) with the above array or biochip comprising one or more of the target DNA genes; d) performing an analysis using the array or biochip of c) to determine the methylation of at least one or more target DNA genes obtained from the sample; and e) comparing the methylation of at least one or more target DNA genes obtained from the sample tissue with the methylation of at least one target DNA gene obtained from a control sample, wherein a detectable increase in the methylation of at least one or more target DNA genes obtained from the sample compared to control is greater than the amount of methylation in the control sample, the target DNA gene is considered to be methylated.

In accordance with one or more embodiments of the present invention, it will be understood that the term "biological sample" or "biological fluid" includes, but is not limited to, any quantity of a substance from a living or formerly living patient or mammal Such substances include, but are not limited to, blood, serum, plasma, urine, cells, organs, tissues, bone, bone marrow, lymph, lymph nodes, synovial tissue, chondrocytes, synovial macrophages, endothelial cells, and skin. In a preferred embodiment the biological sample is a breast tissue sample, and more preferably, a breast tumor tissue sample.

The term "DNA target site" or "target DNA gene" as used herein, means one or more regions of the target gene that are analyzed for CpG methylation.

It will be understood by those of ordinary skill, that there are a number of ways to detect DNA methylation, and these are known in the art. Examples of preferred methods of detection of methylation of DNA in a sample include the use of Quantitative Methylation Specific PCR (Q-MSP), oligonucleotide methylation tiling arrays, paramagnetic beads linked to MBD2, i.e., BeadChip assays and HPLC/MS methods. Other methods include methylation-specific multiplex ligation-dependent probe amplification (MS-MPLA), bisulfate sequencing, and assays using antibodies to DNA methylation, i.e., ELISA assays. The methylation state or GDMI information gathered from these methods can be generated using any type of microprocessor or computing device. In accordance with a preferred embodiment, the method for detection of DNA methylation used is QM-MSP.

As used herein, the term "methylation state" means the detection of one or more methyl groups on a cytidine in a target site of the DNA in the sample.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

It will be understood that the methods of the present invention which determine the methylation state of a target gene or target gene loci in a sample of DNA are useful in preclinical research activities as well as in clinical research in various diseases or disorders, including, for example, cancer.

In an embodiment, the present invention provides a method for determining the methylation status of a breast tissue sample from a subject comprising: a) obtaining a biological sample comprising DNA from the breast tissue of the subject; b) extracting DNA from the sample of a); c) performing methylation analysis on DNA of b) to determine the methylation of at least two or more target DNA genes on at least two or more target DNA genes selected from the group consisting of ACADL, ADAMTSL1, ARFGAP3, B3GAT1, CDCA7, FAM78A, FAM89A, FLJ31951

(RNF145), FLJ34922 (SLFN11), GAS6, HAAO, HEY2, HOXB9, ITGA11, NETO2, PROX1, PSAT1, RECK, SMOC1, SND1, TNFSF9, ADHFE1, DYNLRB2, HSD17B8, PDXK, PISD, WNK4, EVI1, ETS1, IRF7, LYN, PTGS2 (COX2), RUNX3, VIM, DAB2IP, HSD17B4, PER1, and PDXK; d) comparing the amount of methylation on at least two or more target DNA genes in the sample from the subject to the amount of methylation of two or more target DNA genes in a control sample, wherein when the amount of methylation of at least two or more target DNA genes in the sample from the subject is greater than the amount of methylation of at least two or more target DNA genes in the control sample, the target DNA genes are considered to be methylated.

Methods of diagnosis are also provided. The methods comprise detecting a methylation state of one or more target genes discussed above in a biological sample. The sample may be derived from a subject, preferably from a breast tumor from a subject. Diagnosis of a disease state in a subject may allow for prognosis and selection of therapeutic strategy.

It will be understood by those of ordinary skill, that a diagnosis of ER+ breast cancer can be made by detection of increased methylation of one or more of the following target genes: ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, and TNFSF9 as they were found hypermethylated almost exclusively in ER+ tumors.

It will also be understood by those of ordinary skill, that a diagnosis of ER− breast cancer can be made by detection of increased methylation of one or more of the following target genes: ADHFE1, DYNLRB2, LYN HSD17B8, PDXK, PISD, and WNK4, because they were found hypermethylated almost exclusively in ER− tumors.

Moreover, a diagnosis of ER− breast cancer can be made by detection of increased methylation of two, or three, or more of the following target genes: DAB2IP, HSD17B4, and PER1, in addition to the genes noted above, because they were also found hypermethylated almost exclusively in ER− tumors.

In accordance with one or more embodiments of the present invention, it will be understood that the types of cancer diagnosis which may be made, using the methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream. The cancer can be an epithelial cancer. As used herein the term "epithelial cancer" refers to an invasive malignant tumor derived from epithelial tissue that can metastasize to other areas of the body, e.g., a carcinoma. Preferably, the epithelial cancer is breast cancer. The cancer can be a non-epithelial cancer. As used herein, the term "non-epithelial cancer" refers to an invasive malignant tumor derived from non-epithelial tissue that can metastasize to other areas of the body.

The phrase "controls or control materials" refers to any standard or reference tissue or material that has not been identified as having cancer.

The nucleic acids used as primers in embodiments of the present invention can be constructed based on chemical synthesis and/or enzymatic ligation reactions using procedures known in the art. See, for example, Sambrook et al. (eds.), *Molecular Cloning, A Laboratory Manual*, 3$^{rd}$ Edition, Cold Spring Harbor Laboratory Press, New York (2001) and Ausubel et al., *Current Protocols in Molecular Biology*, Greene Publishing Associates and John Wiley & Sons, NY (1994). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleotide sequences used herein are those which hybridize under stringent conditions preferably hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C.

The term "isolated and purified" as used herein means a protein that is essentially free of association with other proteins or polypeptides, e.g., as a naturally occurring protein that has been separated from cellular and other contaminants by the use of antibodies or other methods or as a purification product of a recombinant host cell culture.

The term "biologically active" as used herein means an enzyme or protein having structural, regulatory, or biochemical functions of a naturally occurring molecule.

The term "reacting" in the context of the embodiments of the present invention means placing compounds or reactants in proximity to each other, such as in solution, in order for a chemical reaction to occur between the reactants.

As used herein, the term "treat," as well as words stemming therefrom, includes diagnostic and preventative as well as disorder remitative treatment. The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, screening, or other patient management, including treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

In an embodiment, the present invention provides a method for predicting poor treatment outcome in a subject having breast cancer comprising: a) obtaining a biological sample comprising DNA from the breast tissue of the subject; b) extracting DNA from the sample of a); c) performing methylation analysis on DNA of b) to determine the methylation of at least one or more target DNA genes selected from the group consisting of TMEM179, CRMP1 and SCNN1B in ER+ breast tumor tissue, or c) detecting the amount of methylation of at least one or more target DNA genes selected from the group consisting of ALX1, CDO1, COL14A1, EPHA5, EYA4, FLRT2, GPX7, KCNB2, *LAMA*1, LHX1, LHX2, NEUROG1, POU3F2, TMEFF2 and STMN3 in ER− breast tumor tissue, or d) detecting the amount of methylation of at least one or more target DNA genes selected from the group consisting of AKR1B1, COL6A2, EYA4, GPX7, HOXA13, HOXB13, NKX6-2, NRP2, POU4F2, REM1, and SLITRK3 in both ER+ or ER− breast tumor tissue; e) comparing the amount of methylation of at least one or more target DNA genes in the sample from the subject to the amount of methylation of at least one or more target DNA genes in a control sample; wherein when methylation is detected on one or more target DNA genes from c) or d) and/or e) the subject is diagnosed as having a high likelihood of recurrent breast cancer.

As used herein, the term "poor treatment outcome" or "poor prognosis" means that tumors having one or more of the above genes methylated have been shown to have a high likelihood of recurrence after initial treatment. This can include tumors which are resistant to radiation, chemotherapy, surgery and combinations of two or more of these types of treatments. While not being limited to any particular theory, these results of the present invention, discussed herein, support the finding that highly methylated homeobox loci and loss of their expression may likely contribute to poor outcome in breast cancer.

A kit is also provided comprising an array of oligonucleotides as described herein, or portions or fragments thereof, as well as a biochip as described herein, along with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

EXAMPLES

Tissues. Frozen breast cancer tissues that were excised from patients with Stage 1-3 disease prior to treatment (n=103) were retrieved from Surgical Pathology at Johns Hopkins Hospital (Baltimore, Md.) and confirmed to contain >50% epithelial cells. Normal breast organoids were prepared by enzymatic digestion of reduction mammoplasty specimens (n=15; median patient age=52 years, range 47 to 71). Normal ducts from breast tissue >2 cm away from the tumor (n=6) were isolated from cryosections using laser-capture micro-dissection (PALM MicroBeam, Carl Zeiss Microimaging, North America). The studies were done with institutional review board approval. Tumor characteristics are provided in Table 1.

TABLE 1

Characteristics of the ER+/PR+ and ER−/PR− primary breast cancer patients in the study

| Characteristics* | ER+ (N = 44) | ER− (N = 38) |
|---|---|---|
| Recurrences | 7 | 11 |
| DFS at 5 yrs (Estimated by Kaplan-Meier) | 87% | 71% |
| HER2+/ # cases annotated | 4/20 | 10/25 |
| Median % Ki67 | 20 | 50 |
| AJCC Stage | | |
| I | 7 | 4 |
| II | 22 | 19 |
| III | 15 | 15 |
| Median Tumor size (mm) | 28 | 59 |
| Having <1 mm margin | 10 | 7 |
| Therapy** | | |
| Locoregion Therapy | 3 | 11 |
| Endocine | 0 | 2 |
| Hormone | 34 | 0 |
| Chemotherapy | 21 | 27 |

*DFS: Disease-Free Survival, or total follow-up in No Progression cases; mo: months; AJCC: American Joint Commission on Cancer.
**Therapies add up to more than totals because of cases with both E (Endocrine) & C (Chemotherapy); LR: locoregional therapy only (surgery ± radiation).
A total of 21 additional samples were arrayed and used for ER classification, but not for outcome analyses. These 21 cases were excluded from the outcome analysis for the following reasons: Neoadjuvant treatment
(n = 8); Samples obtained 6 months after the initial diagnosis (n = 10); progression within 6 month after diagnosis (n = 10).

Genomic DNA extraction, sodium bisulfite conversion and quality assurance. DNA extraction and quality assurance were performed as described previously (Cancer Res. 2004; 64:4442-52; Biotechniques. 2006; 40:210-9). DNA extractions and proteinase K treatment of fresh frozen tissues were performed as described previously and according to manufacturer's directions. Sodium bisulfite conversion of DNA was done with the EZ DNA methylation Kit (Zymo Research, D5002). Purified DNA 2 µg or lysate from 6-8 tissue sections (10 µm thick) was mixed with 7.5 µl M-dilution buffer in a final volume of 42.5 µl and incubated at 42° C. for 30 minutes. Conversion was accomplished after the addition of 97.5 µl CT Conversion Reagent (prepared by adding 750 µl water and 185 µl M-dilution buffer to a vial of CT Conversion Reagent intended for 10 reactions) and samples were incubated in a thermocycler overnight (95° C. 30 seconds, 50° C. 1 hour, 16 cycles). Bisulfite-converted DNA was column-purified using a ZymoSpin IC column and eluted in 12 ul of water. DNA was quantified using a Nanodrop-1000 and 1 µl of a 1:5 dilution of DNA was tested to insure amplification potential with a panel of markers developed for QM-MSP which overlap array CpG loci (e.g. AKR1B1). Any sample that amplified poorly was not used. (FIG. 1).

Methylome Analysis. Bisulfite-converted DNA was analyzed using Illumina Infinium Human Methylation27 BeadChip Kit (WG-311-1202) in the DNA Microarray Core, Johns Hopkins University. The BeadChip contains 27,578 CpG loci covering more than 14,000 human RefSeq genes.

The methylation of a single CpG is detected with two bead type probes per CpG (recognizing U=unmethylated, and M=methylated DNA) at single-base resolution by using primer extension with a labeled nucleotide in single color. For array, samples were adjusted to 75 ng/µl with water and 4 µl was processed according to manufacturer's directions. Data were extracted using GenomeStudio Methylation Module v1.0 software. The methylation value for each 50 bp CpG locus is expressed as a β-value, representing a continuous measurement from 0 (completely unmethylated) to 1 (completely methylated) according to the following calculation: β value=(signal intensity of M probe)/[(signal intensity of M+U probes)+100]; the average β-value is based on the average intensity of all U and M CpG probes for a given locus. Probe performance is reported as the p-detection value, reflecting the extent of variation among replicates of a single bead type. Only loci with p-detection values <0.0001 were considered. As controls for normal and tumor samples, we used replicate samples of a normal breast organoid (ORG) and a breast cancer cell line MDA-MB-231, (provided by NCI as the ICBP45 breast cancer cell line set through ATCC) with a highly methylated genome.

Test of array reproducibility. Additional replicate samples (two groups of 4 samples each) were used to assess assay reproducibility. Two identical aliquots each of MDA-MB-231 cell line DNA and of ORG DNA were processed independently through sodium bisulfite conversion. Two unrelated tumor samples were microdissected using laser capture, processed to completion with sodium bisulfite and then halved. This resulted in 2 identical groups of 4 samples, MDA-MB-231, ORG, Tumor 1 and Tumor 2. The 8 samples were run together on a HumanMethylation27BeadChip then analyzed. Results showed excellent correlation between groups of samples ($r^2$=0.991; FIG. 1)

Data analysis. T-tests, ANOVA, Wilcoxon rank sum tests and chi-squared tests were used to identify significant association between methylation and such covariates as tumor subtype and ER status. Cox regression was used to model associations between methylation levels and time to recurrence, in the presence of relevant clinical covariates. Associations to binary outcomes were modeled using logistic regression. Where possible, empirical Bayes linear models were used in place of standard t-tests, ANOVA and linear regressions. These methods use modified estimates of variance to reduce false positive rates in the analysis of microarray data. Data were also analyzed using GenomeStudio software (Illumina, Inc., San Diego, Calif.), Bioconductor in R (bioconductor.org), and GraphPad Prism v5.02 (GraphPad Software, San Diego, Calif.; (graphpad.com). For differential analysis, results are reported as DiffScore within GenomeStudio Methylation module, after computing for false discovery (rate 0.05). To convert DiffScore to adjusted p-value: p-value=1/[10^(ABS(DiffScore)/(10)], where p-value of 0.05 is equal to a DiffScore of +/−13, p-value of 0.01 is equal to a DiffScore of +/−20, and p-value of 0.001 is equal to a DiffScore of +/−30. Methylation Score derivation: a methylation score for ER subtype specific markers was derived by calculating the average methylation over all 40 probes, after standardizing the data for each CpG locus by subtracting its mean methylation and dividing by its standard deviation. Hypermethylation at some loci was associated with the ER− phenotype while other loci were hypermethylated in the ER+ samples, so standardized methylation levels for the latter loci were multiplied by −1, so that all 40 genes would vote in the same direction.

Data was analyzed using GenomeStudio software (Illumina, Inc., San Diego, Calif.) and Bioconductor in R (bioconductor.org). Unsupervised cluster analysis was used to visualize and characterize broad methylation patterns in the data. All tests were two tailed and p values of <0.05 were considered significant. Cox regression and Kaplan-Meier plots were used to model associations between methylation levels and time to recurrence, with and without adjustment for relevant clinical covariates, and to identify potential predictive markers. Covariates used were patients' age at diagnosis, tumor grade, pathological T stage, lymph node status, estrogen receptor, progesterone receptor, type of primary surgery (with or without radiotherapy), and adjuvant therapy (chemotherapy and/or endocrine therapy).To identify methylated genes associated with ER status and their biology, a different approach was taken, emphasizing genes in which methylation changed dramatically between ER+ and ER− samples. To achieve this, the initial selection was based on large fold changes. To evaluate the predictive capability of a panel of loci associated with ER status, we used independent samples to perform ROC analysis of a summary score of methylation derived as follows: 1) Methylation at each locus was standardized to have a common scale by subtracting the mean methylation level and dividing by the standard deviation for that locus, so that low methylation resulted in negative values, while high methylation gave positive values. 2) high methylation was associated with ER+ status at some loci, and with ER− status at others, so standardized methylation scores for these latter loci were multiplied by −1, such that a high score uniformly indicated ER+ samples; and 3) Genes were combined by averaging the standardized methylation scores for each patient, and the average score used in ROC analyses. The same procedure was used to summarize multi-locus homeobox panels associated with recurrence.

Validation in TCGA samples. To verify that patterns of methylation observed in association with ER status and risk of recurrence within the JHU cohort were characteristic of breast cancer, data publicly available from the Cancer Genome Atlas Project (TCGA, tcga-data.nci.nih.gov/) was downloaded and analyzed. TCGA was selected to perform this analysis since Illumina Meth27K was used, enabling direct comparisons for the same 50 bp CpG locus probes. In total, 185 samples were available on the Illumina 27k Human Methylation platform, and 465 samples were available on the Agilent G4502A expression array. Time to recurrence was not available at the time of download, but time to death was obtained for 342 of the samples queried on expression array and 182 samples queried on methylation array. Probe level data (TCGA level 2) was obtained for the methylation platform while gene-level summaries (TCGA level 3) were used for RNA expression. Rank-based Spearman correlations were calculated between methylation and expression using the 182 samples. Each methylation probe was mapped to the nearest gene using the open source Illumina methylation platform annotation package available from Bioconductor (bioconductor.org/packages/2.6/data/annotation/html/IlluminaHumanMethylation27k.db.html), and correlations calculated for probes mapping to genes found on the expression array. Benjamini-Hochberg adjusted p-values are reported for each probe, alongside the correlation coefficient. Association between overall survival and methylation or expression was evaluated by Cox regression. The ability of molecular markers to predict ER status was measured by performing an ROC analysis using the methylation and expression levels of individual genes as predictors and reporting the area under the ROC curve. For expression, the ROC analysis was based on the expectation of an inverse relationship between methylation and expression, so that in some cases, where a significant, positive association is observed between the two platforms, the area under the ROC may be substantially less than 0.5.

QM-MSP (Quantitative-Multiplex Methylation-Specific PCR). Details of this method have been reported previously (Cancer Research. 2009; 15:3802-11; Biotechniques. 2006; 40:210-9; Cancer Res. 2004; 64:4442-52). Briefly, sodium bisulfite converted template DNA is pre-amplified by PCR with gene-specific forward and reverse primers, hybridizing to regions lacking CpG residues and up to 12 genes are co-amplified with amplicons ranging to 300 bp. QM-MSP primers were designed to overlap array CpG loci. An aliquot of this reaction is diluted between 1:5 and 1:10,000 with water and then used as template for real-time methylation-specific PCR which was performed on an Applied Biosystems 7500 system. Separately for each gene, the copy number of methylated and unmethylated alleles is determined by absolute quantitation in a single well using two-color fluorescent labeling. The relative amount of methylation is calculated as % M=100×[no. of copies of methylated DNA/(no. of copies of methylated+unmethylated DNA)]. Cumulative methylation of a panel of genes is calculated as the sum of the % of each gene, where 10 genes in a panel would have a maximal possibility of 1000 cumulative methylation units per sample. Concordant quantitative methylation levels are observed between the Human Methylation27 BeadChip array and QM-MSP on primary tumors for AKR1B1 (FIG. 4C). AKR1B1 primers and probes: AKR1B1_F_Ext: gYGtaattaattagaaggtttttt, (SEQ ID NO:1), AKR1B1_R_Ext: aacacctaccttccaaatac, (SEQ ID NO: 2), AKR1B1_FM: gCGCGttaatCGtaggCGttt, (SEQ ID NO: 3) AKR1B1_RM: cccaataCGataCGaccttaac, (SEQ ID NO: 4) AKR1B1_FUM: TGgTGTGttaatTGtaggTGtttt, (SEQ ID NO: 5) AKR1B1_RUM: cccaataCAataCAaccttaacC, (SEQ ID NO: 6) AKR1B1_M_probe: VIC-CGtaccttttaaataaccCG-taaaatCGa-TAMRA (SEQ ID NO: 7), and AKR1B1_U_Probe: 6FAM-ACAtacctttaaataaccCAtaaaat-CAac-TAMRA (SEQ ID NO: 8).

Example 1

Methylation Profiling of Primary Invasive Breast Cancer Tumors. Whole-genome methylation array analysis was performed using the Illumina Infinium HumanMethylation27 BeadChip with primary invasive carcinoma samples (n=103), samples from microdissected normal breast tissue distant from the primary tumor (n=6), and epithelium enriched organoids isolated from normal breast (n=15). The array quantifies the proportion of methylated cytosines ($^5$mC) to total cytosines at each of 27,578 different CpG dinucleotides. The steps followed for the analysis is shown as a flowchart in FIG. 2.

Figures 2A, 2B:
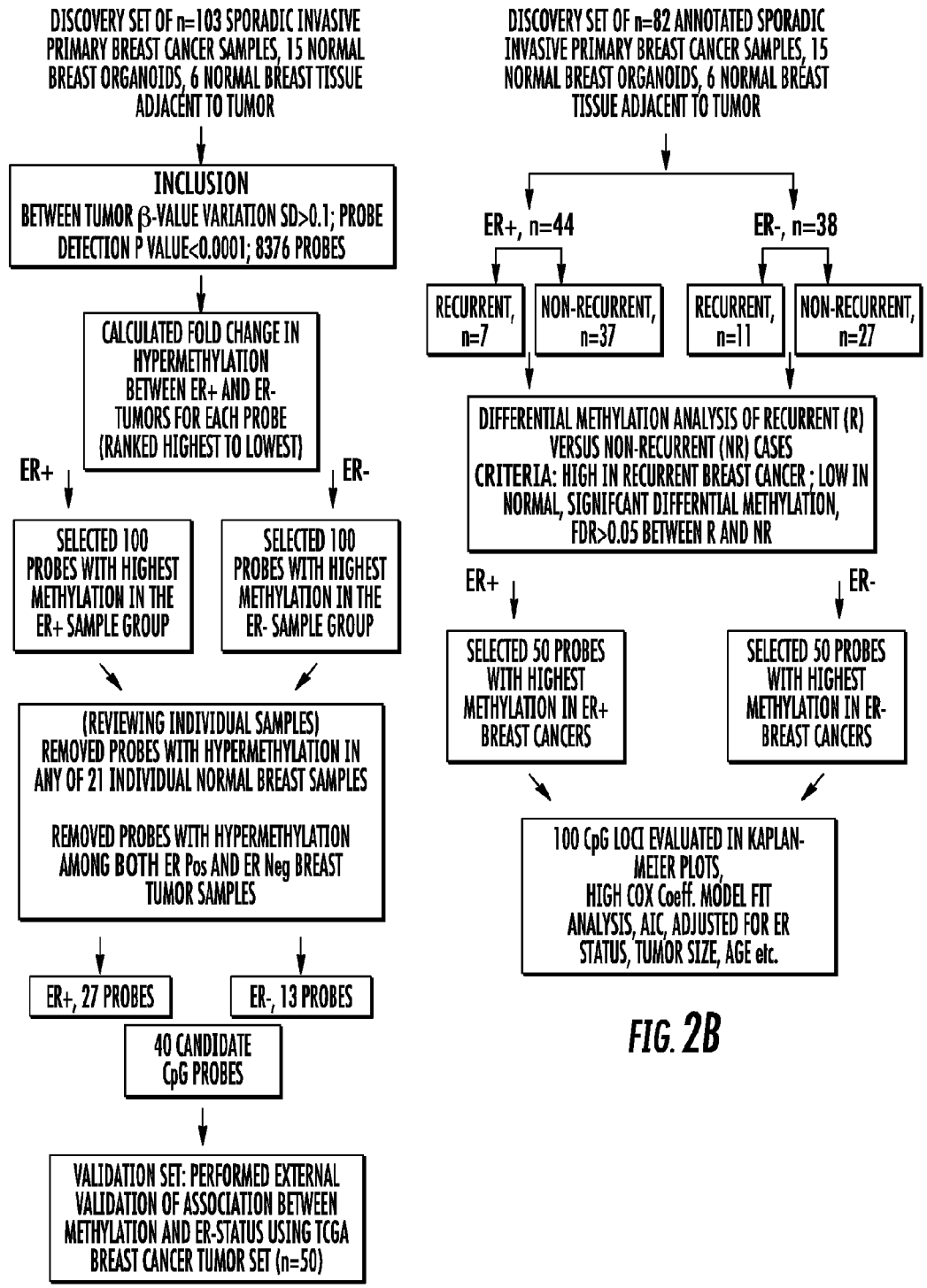
FIG. 2 illustrates the schema outlining study design for analysis of association of methylation with (A) ER-status and (B): disease outcome.

To characterize the overall methylation profile of primary invasive breast tumors, unsupervised hierarchical cluster analysis using the Manhattan distance was performed on the most varied probes across tumors (1378 gene loci, SD>1.60) (FIG. 2A). Two distinct clusters of tumors were observed. Cluster 1 was enriched for ER+ breast cancer (21/28; 75%), while Cluster 2 contained 85% of the ER− tumors (41/75; 55% of total). Given the importance of ER in breast cancer, it is not surprising to observe a strong association between predominant methylation patterns and ER status (odds ratio=3.57, 95% C.I=1.27-11.20, p-value=0.082), but the result also highlights the importance of gene methylation in the disease process. The data also suggested additional subgroups within Clusters 1 and 2 with distinct methylation profiles such as Cluster 2B, which contains all ER-PR+ tumor samples.

Example 2

Distinct groups of genes are specifically and recriprocally hypermethylated in ER+ versus ER− breast cancer.

Figure 3:
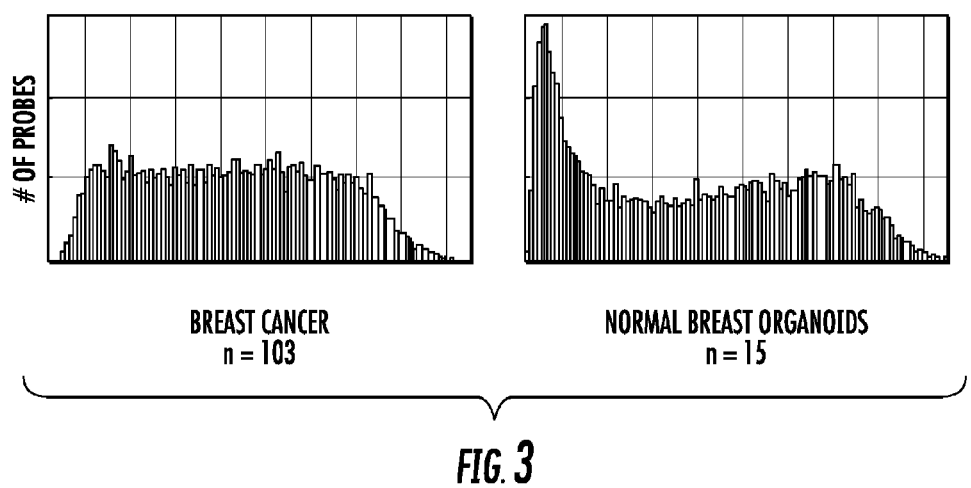
FIG. 3 shows the determination of the differences in breast cancer biology/behavior between ER subtypes. Methylation patterns were characterized at 8376 selected CpG loci according to ER status. The graphs show the distribution of methylation among these loci.
Figure 4:
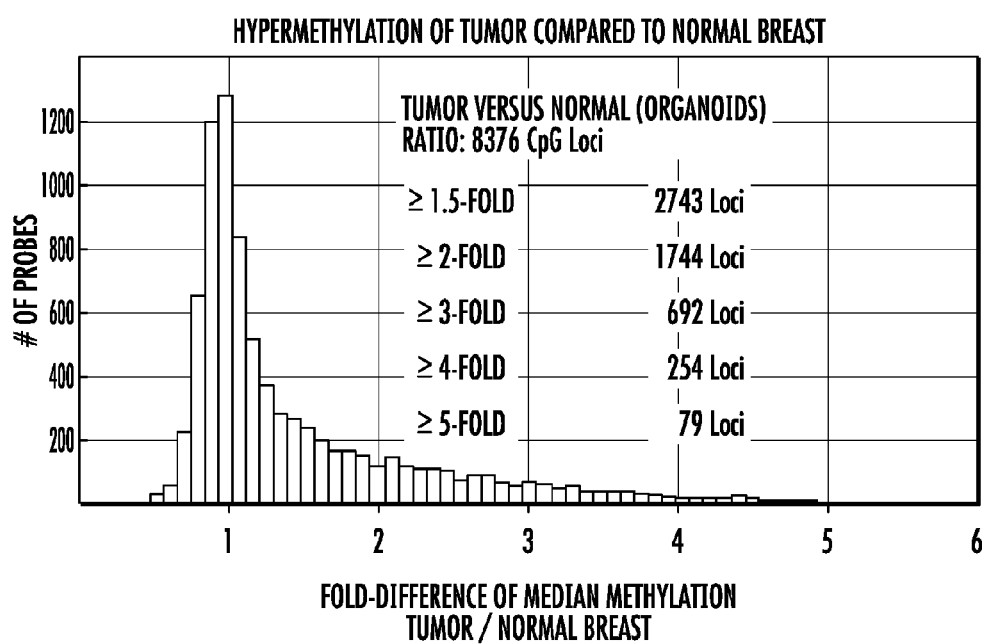
FIG. 4 is another histogram showing the majority of loci were more highly methylated in tumor than in normal organoid samples; 1744 loci in tumors had median methylation more than 2-fold higher compared to normal organoids.

Very little is known about the genomic features within each ER subtype of breast cancer that could explain why some patients have a good outcome while others will do poorly regardless of treatment. To determine the differences in breast cancer biology/behavior between ER subtypes, methylation patterns were characterized at 8376 selected CpG loci according to ER status. These loci met two criteria: 1) showed the most variation across primary tumors (SD >0.100) and 2) had probe detection p-values <0.0001 (indicating that DNA from that locus was present above background levels and that probe intensities were consistently measured across replicate beads; the distribution of methylation among these loci is shown in FIG. 3). A substantial number of loci were observed with median methylation levels ≥0.15 in both groups of tumor and normal breast organoids. However, the majority of loci were more highly methylated in tumor than in normal organoid samples; 1744 loci in tumors had median methylation more than 2-fold higher compared to normal organoids (FIG. 4).

Figure 5:
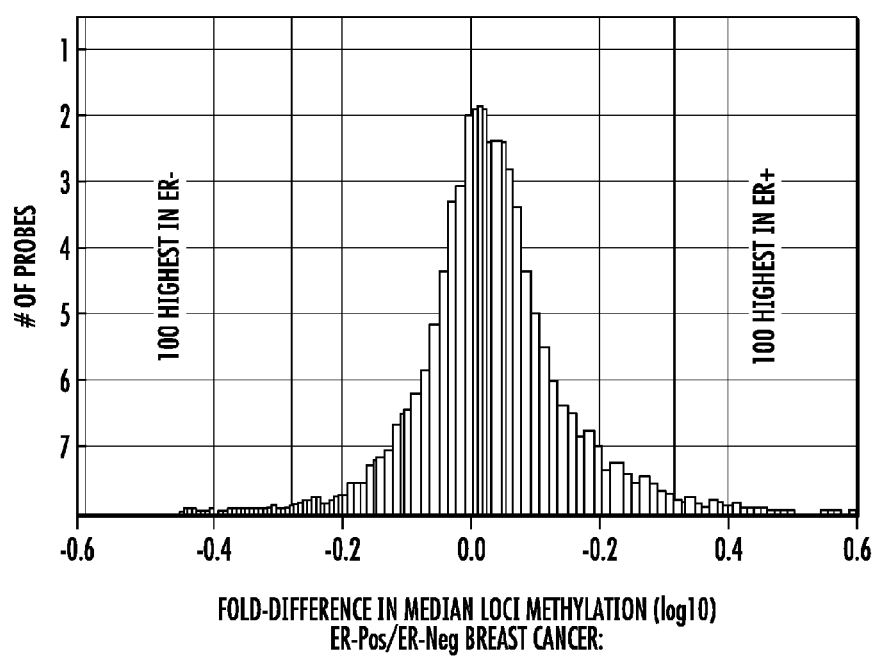
FIG. 5 is a histogram depicting how the top 100 hypermethylated CpG loci in each group of ER-positive and ER-negative tumors were selected.
Figure 6:
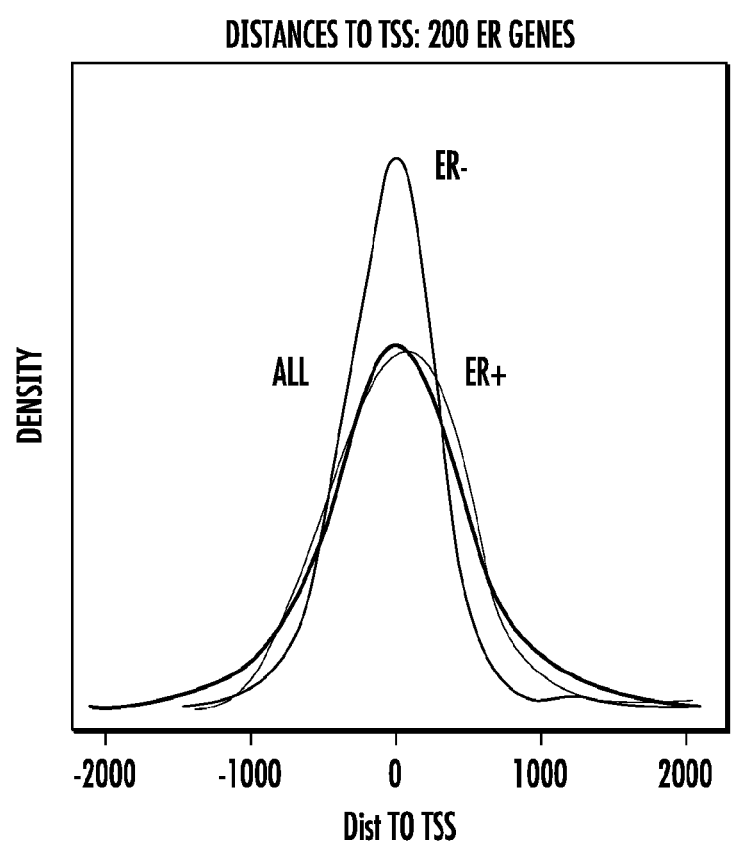
FIG. 6 is a histogram showing that ER-negative tumors had a higher number of hypermethylated loci located closer to the transcriptional start site (TSS), compared to ER-positive tumors, or to the 8376 array loci as a whole.

ER+ tumors were found to have a higher frequency of hypermethylated gene loci compared to ER− tumors (FIG. 5). Methylation at 5264 loci was higher (ratio >1) in ER+ tumors samples, compared to methylation of 3112 loci (ratio <1) in ER− tumors. The top 100 hypermethylated CpG loci in each group of ER+ and ER− tumors were selected (FIG. 5; ER− loci=ratio 0.52-0.15 and ER+ loci=ratio 3.98-2.23). Interestingly, ER− tumors had a higher number of hypermethylated loci located closer to the transcriptional start site (TSS), compared to ER+ tumors, or to the 8376 array loci as a whole (FIG. 6). This finding suggested a more rigorous suppression of gene expression by methylation in the ER− subtype, since methylated regions overlapping the TSS have been shown to most tightly negatively regulate transcription.

To further refine this set to identify ER subtype-specific biological/molecular functions most driven by the epigenome in breast cancer, we selected a subgroup of 40 hypermethylated loci of the the 200 CpG locus set that individually showed the highest subtype specificity in individual tumor samples. Each individual locus was selected whose methylation profile demonstrated 1) robust reciprocal methylation between the two ER subtypes, 2) an incidence >20% of methylation within the breast cancer subtype and 3) low methylation in normal breast epithelium/stroma and leukocytes (β-value <0.15; data not shown). Using these selection criteria, in the discovery set, 27 loci/probes were identified as aberrantly and reciprocally hypermethylated in ER+ tumors and identified 13 loci/probes aberrantly hypermethylated in ER− tumors. The majority of these were at loci newly identified as hypermethylated in breast cancer, and some never observed before as hypermethylated in cancer (Table 2).

TABLE 2

Hypermethylated Loci Newly Identified in Breast Cancers

| Gene symbol | Identified in this study | Hyper-Methylated in other cancers | Known aberrant expression | Gene | Location |
|---|---|---|---|---|---|
| ACADL | ER-POS | NO | NO | acyl-CoA dehydrogenase, long chain | Cytoplasm |
| ADAMTSL1 | ER-POS | NO | NO | ADAMTS-like 1 | Extracellular |
| ARFGAP3 | ER-POS | NO | NO | ADP-ribosylation factor GTPase | Cytoplasm |
| B3GAT1 | ER-POS | NO | NO | beta-1,3-glucuronyltransferase 1 | Cytoplasm |
| | | | | cell division cycle associated 7 | Nucleus |
| FAM78A | ER-POS | NO | NO | family with sequence similarity 78, | unknown |
| FAM89A | ER-POS | NO | NO | family with sequence similarity 89, | unknown |
| FLJ31951 | ER-POS | NO | BASAL (37) | unknown | unknown |
| FLJ34922 | ER-POS | NO | NO | schlafen family member 11 | Nucleus |
| GAS6 | ER-POS | NO | NO | growth arrest-specific 6 | Extracellular |
| HAAO | ER-POS | NO | NO | 3-hydroxyanthranilate 3,4-dioxygenase | Cytoplasm |
| HEY2 | ER-POS | NO | NO | hairy/enhancer-of-split related with | Nucleus |
| HOXB9 | ER-POS | NO | NO | homeobox B9 | Nucleus |
| ITGA11 | ER-POS | NO | NO | integrin, alpha 11 | Plasma |
| NETO2 | ER-POS | NO | NO | neuropilin (NRP) and tolloid (TLL)-like 2 | unknown |
| PROX1 | ER-POS | NO | NO | prospero homeobox 1 | Nucleus |
| PSAT1 | ER-POS | NO | BASAL (37) | phosphoserine aminotransferase 1 | Cytoplasm |
| RECK | ER-POS | YES | NO | reversion-inducing-cysteine-rich protein | Plasma |
| SMOC1 | ER-POS | NO | NO | SPARC related modular calcium binding | Extracellular |
| SND1 | ER-POS | NO | NO | staphylococcal nuclease and tudor domain | Nucleus |
| TNFSF9 | ER-POS | YES | NO | tumor necrosis factor (ligand) | Extracellular |
| ADHFE1 | ER-NEG | YES | NO | alcohol dehydrogenase, iron containing, 1 | unknown |
| DYNLRB2 | ER-NEG | NO | NO | dynein, light chain, roadblock-type 2 | Cytoplasm |
| HSD17B8 | ER-NEG | NO | NO | hydroxysteroid (17-beta) dehydrogenase 8 | Cytoplasm |
| PISD | ER-NEG | NO | NO | phosphatidylserine decarboxylase | Cytoplasm |
| PDXK | ER-NEG | NO | NO | Pyridoxal kinase (vitamin B6 kinase) | Cytoplasm |
| WNK4 | ER-NEG | NO | NO | WNK lysine deficient protein kinase 4 | Plasma |

The genes ACADL, ADAMTSL1, ARFGAP3, B3GAT1, CDCA7, FAM78A, FAM89A, FLJ31951 (RNF145), FLJ34922 (SLFN11), GAS6, HAAO, HEY2, HOXB9, ITGA11, NETO2, PROX1, PSAT1, RECK, SMOC1, SND1, and TNFSF9 were found hypermethylated almost exclusively in ER+ tumors while, ADHFE1, DYNLRB2, HSD17B8, PDXK, PISD and WNK4 were found hypermethylated in ER− tumors. A number of genes previously reported as having subtype-specific methylation were also identified. EVI1, ETS1, IRF7, LYN, PTGS2 (COX2), RUNX3, and VIM were found to be hypermethylated in ER+ tumors, while DAB2IP, HSD17B4, and PER1 were reported to be hypermethylated in ER− breast cancers (detailed information in FIGS. 9 and 10 and Table 3).

A second distinct CpG locus of PDXK was previously found hypermethylated in ER+ breast cancers. There was not found any gene that was preferentially methylated in ER+ or ER− tumors where the literature conflicted with the data of the present invention. Thus, many novel and some published gene loci were discovered that showed tumor-specific and ER subtype specific hypermethylation. Existing literature provided further validity to the present invention.

Example 3

External validation of methylation array findings in an independent test set of primary tumors. The findings of the present invention were validated in publicly available data

TABLE 3

Hypermethylated Loci Previously Identified in Breast Cancers

Figure 7:
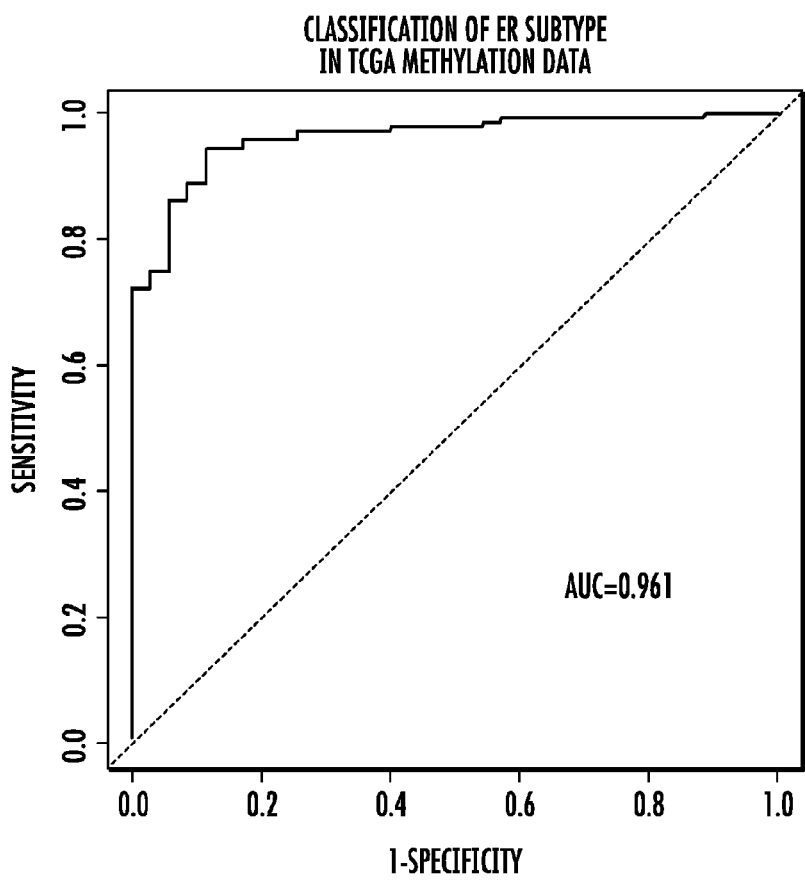
FIG. 7 is a ROC graph. To evaluate the predictive performance of the 40 locus panel, an average methylation score was derived for the entire set as described. Using this score ROC analysis demonstrated a high classification accuracy for the ER-subtype in TCGA data with an area under the ROC curve of 0.961, with a specificity of 89% at a sensitivity of 90%.

| Gene symbol | Published | Hyper methylated in other cancers | Known aberrant expression | Gene | Location |
|---|---|---|---|---|---|
| EVI1 | ER-POS | NO | BASAL | MDS1 and EVI1 complex locus | Nucleus |
| ETS1 | ER-POS | | BASAL | v-ets erythroblastosis virus E26 | Nucleus |
| IRF7 | ER-POS | YES | | interferon regulatory factor 7 | Nucleus |
| LYN | ER-POS | YES | BASAL | v-yes-1 Yamaguchi sarcoma viral | Cytoplasm |
| PDXK | ER-POS | NO | NO | pyridoxal kinase (vitamin B6 | Cytoplasm |
| PTGS2 | ER-POS | YES | BASAL | prostaglandin-endoperoxide | Cytoplasm |
| RUNX3 | ER-POS | YES | BASAL | runt-related transcription factor 3 | Nucleus |
| VIM | ER-POS | YES | BASAL | vimentin | Cytoplasm |
| DAB2IP (4 | ER-NEG | YES | | DAB2 interacting protein | Plasma |
| HSD17B4 | ER-NEG | YES | ER POS | hydroxysteroid (17-beta) | Cytoplasm |
| PER1 | ER-NEG | | | period homolog 1 (*Drosophila*) | Nucleus | on the breast cancer samples in TCGA (tcga-data.nci.nih.gov/) using an ROC analysis to evaluate predictive ability. The median area under the ROC curve for the 200 loci was 0.7; and one gene, SERPINA12, had an AUC of 0.95. In all, 156/200 ER probes yielded AUCs higher than 0.563, a range in which we expect only 5% of CpG loci by chance alone. Interestingly, expression of most of these same genes is also a very strong predictor of ER status. It was found that 121 of the 175 unique genes from the ER panel of the present invention and available on the expression array had areas under the curve exceeding the same 5% threshold. This is consistent with the high degree of correlation observed between expression and methylation measurements of these genes in the TCGA data. At an FDR of 0.05, 142 of 200 CpG loci are significantly inversely correlated with expression. The TCGA data provided support for the existence of ER subtype-specific methylation in breast cancer. To evaluate the predictive performance of the 40 locus panel of the present invention (FIG. 7), an average methylation score was derived for the entire set as described in the Methods. Using this score ROC analysis demonstrated a high classification accuracy for the ER subtype in TCGA data with an area under the ROC curve of 0.961, with a specificity of 89% at a sensitivity of 90% (FIG. 7). A similar composite score derived from expression probes for the same genes showed some discriminatory ability in the TCGA data, albeit reduced, with an area under the ROC of 0.667 (data not shown).

Example 4

CpG loci associated with disease progression in patients with newly diagnosed invasive breast cancer. To develop an epigenomic signature that predicts outcome in patients with breast cancer, differential methylation analysis was conducted on primary tumors from recurrent versus non-recurrent breast cancers. A subgroup of 82 well-annotated, invasive breast tumors derived from the discovery set of 103 tumors that included 44 ER+(7 recurrences) and 38 ER− (11 recurrences) breast cancers was used, and independently queried the ER+ and ER− tumor groups (Table 1) as follows. Differential methylation analysis was performed in GenomeStudio, using the DiffScore algorithm to compare tumors which later recurred to those which did not recur. The analysis was performed separately on the ER+ and ER− tumor groups. Candidate loci (50 per ER subtype) were selected meeting 3 criteria: 1) more highly methylated in recurrent tumors than in non-recurrent tumors, 2) relatively unmethylated in normal samples ($\beta<0.15$), and 3) significantly differentially methylated above the false discovery rate cutoff (5%). Next a multivariate Cox regression analysis was performed for each of these candidate loci and generated Kaplan-Meier plots, showing the interrelationships between ER status and methylation and depicted in these plots as high/low with respect to the median methylation level for each CpG locus. From these 100 candidate CpG loci, a set of 32, selected for high Cox coefficients, and visually striking Kaplan-Meier plots (data not shown) were followed up most closely, including with an extensive literature search to identify previous associations with outcome in breast cancer. Novel associations with poor outcome were identified for 1) TMEM179, CRMP1 and SCNN1B in ER+ breast cancer, 2) ALX1, CDO1, COL14A1, EPHA5, EYA4, FLRT2, GPX7, KCNB2, LAMA1, LHX1, LHX2, NEUROG1, POU3F2, TMEFF2 and STMN3 in ER− breast cancer, and 3) AKR1B1, COL6A2, EYA4, GPX7, HOXA13, HOXB13, NKX6-2, NRP2, POU4F2, REM1, and SLITRK3, in both ER+ and ER− tumors (FIG. 8). Since the differential methylation analysis was designed in such a way to find loci most highly methylated in recurrent tumors, there was no observation of hypomethylated loci associating with recurrence.

Figure 11:
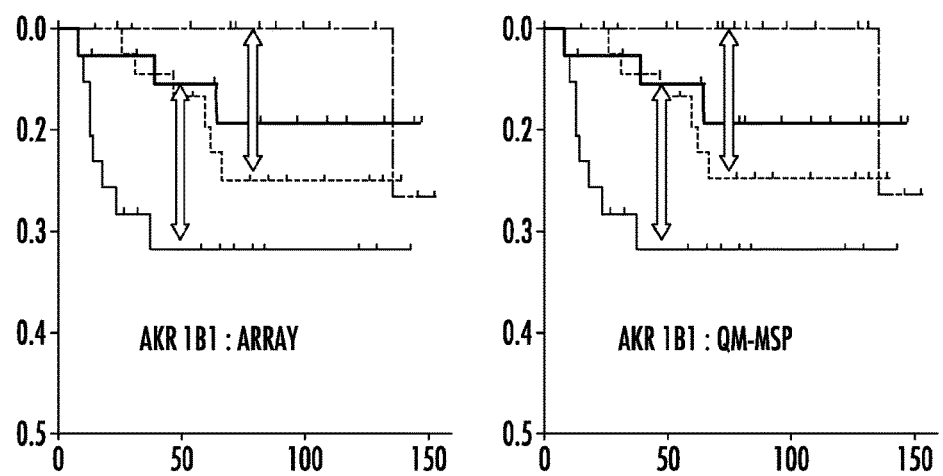
FIG. 11 depicts A comparison of level of methylation in AKR1B1 assessed by the array and by QM-MSP in individual primary tumors, and both data plotted as Kaplan-Meier plots.

To verify array data using an independent assay, and to ensure future technical translation of the HumanMethylation27 array data to laboratory assays, several methylated genes, such as EVI1, DAB2IP and AKR1B1 were tested by performing QM-MSP. In each case, an excellent correlation was observed between the levels of gene methylation assessed by both assays. A comparison of level of methylation in AKR1B1 assessed by the array and by QM-MSP in individual primary tumors, and both data plotted as Kaplan-Meier plots in shown in (FIG. 11).

A striking observation was that nearly 20% of the recurrence loci (18/100 loci; 15/91 unique genes) were from homeobox-containing genes including the HOX, LHX, POU, ALX and NK6 gene families (data not shown). With only 375 homeobox loci (189 genes) present in the 27,578 loci (14,495 genes) array, this represented a dramatic enrichment of homeobox genes in our 100 loci recurrence related set (odds ratio=16.17, p=6.515e-13). These data clearly implicate methylated homeobox genes as key factors in tumor progression. To determine if the other homeobox loci on the array exhibited similar methylation patterns, the analysis was extended to 60 homeobox loci which showed high variance (SD above the 95th percentile for the array) among the tumors, excluding the 18 loci represented in the recurrence sets. 2D-hierarchial cluster analysis (using the Manhattan distance) was performed to characterize these loci. The 18 homeobox gene loci derived from the 100 recurrence locus set have distinctive methylation patterns, showing significant co-methylation within the first cluster, with highly methylated samples tending to be methylated for all the loci. Interestingly, a similar clustering profile was observed with the 60 homeobox loci, suggesting that the homeobox genes as a group have a common methylation signature. To evaluate correlation with recurrence, we derived an average methylation score for the panel as described above. In a multivariate analysis that included age, stage, treatment and ER status, there was clear evidence of a significant additional and independent contribution to the model where the Cox coefficient was 1.74, with a p-value of 0.0042. Kaplan-Meier plots for the 18 and the 60 homeobox loci (but not for all 1378 CpG loci that showed differential methylation across all the tumors) illustrate their predictive value. These results support the notion that highly methylated homeobox loci and loss of their expression may likely contribute to poor outcome in breast cancer.

Example 5

External validation of associations with outcome, in an independent test set of primary tumors. Next, validation of these findings was sought in publicly available TCGA breast cancer samples (tcga-data.nci.nih.gov/), using Cox regression to evaluate association between methylation and overall survival; progression free survival was not available for these samples at the time of download. In total, survival information was available for 342 of the samples available on expression array, of which 182 were also available on methylation array. Despite the change of outcome variable and moderate sample sizes, results in TCGA data as a set confirmed the findings that these genes are significantly associated with outcome. An overwhelming majority of the recurrence marker loci (78/100) have positive Cox regression coefficients, indicating that hypermethylation of these loci is associated with a worse outcome in these samples as well. By comparison, one would expect only half of these loci to have positive Cox coefficients by chance alone, giving a composite p-value of 2.2e-09, in support of the association. Additional confirmation for the panel is provided by the fact that for more than ⅔ of these genes, Cox regression analysis of TCGA expression data shows that low expression correlates with worse outcome. This result is wholly consistent with the observed methylation results, and statistically significant in its own right, with a p-value of 0.00022. This is also consistent with the high degree of correlation observed between expression and methylation measurements of these genes in the TCGA data. At an FDR of 0.05, 43 of 100 CpG loci are significantly inversely correlated with expression. A multivariate Cox regression analysis was also performed for each of these candidate loci and Kaplan-Meier plots were generated for the sets of 18 loci (log rank test p-value 0.00027) and 60 loci (log rank test p-value 0.00036), compared to the top 5% of varied probes (1378 probes, p-value 0.112), demonstrating significant interrelationships between homeobox gene methylation and survival (data not shown).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treatment of a subject having breast cancer, the method comprising the steps of:
   (a) extracting DNA from a biological sample comprising DNA from breast cancer tissue from the subject;
   (b) performing bisulfite modification to the DNA in (a);
   (c) contacting the DNA from (b) with a platform comprising an array of oligonucleotide probes for identifying specific methylated target DNA gene loci in a sample, comprising two oligonucleotide probes that each selectively bind the specific methylated loci in the target DNA genes ADAMTSL1 at locus cg00116234 and ARFGAP3 at locus cg00079563 wherein the probes are immobilized on the platform; or,
   (d) contacting the DNA from (b) with a platform comprising an array of oligonucleotide probes for identifying specific methylated target DNA gene loci in a sample, comprising two oligonucleotide probes that each selectively bind the specific methylated loci in the target DNA genes ADHFE1 at locus cg08090772 and PDXK at locus cg23178308;
   (e) providing a non-neoplastic control breast tissue sample; and performing steps (b)-(d) on the control breast tissue sample;
   (f) comparing the methylation of the two target DNA gene loci in the suspect sample from the subject to the methylation of the two target DNA gene loci in the control breast tissue sample;

(g) detecting that the level of methylation of the target DNA gene loci from (c) is greater than the level of methylation of the target DNA gene loci from (e), identifying said human subject as having ER+ breast cancer, and (h) administering to the subject treatment comprising surgery, radiation, and chemotherapeutic treatment with adjuvant endocrine therapy or continuing said treatment; or (i) detecting that the level of methylation of the target DNA gene loci from (d) is greater than the level of methylation of the target DNA gene loci from (e), identifying said human subject as having ER− breast cancer, and (j) administering to the subject treatment comprising surgery and radiation.

2. The method of claim 1, wherein the methylation level of the target DNA gene loci is measured using a BeadChip.

3. The method of claim 1, wherein at step c) the platform further comprises an additional oligonucleotide probe that selectively binds the specific methylated locus in the target DNA gene ACADL at locus cg09068528; or wherein at step d) the platform further comprises additional oligonucleotide probes that selectively bind the specific methylated loci in the target DNA gene DAB2IP at loci cg27650175, cg14063008, cg07981910, and cg05684891.

4. The method of claim 1, wherein at step c) the platform further comprises an additional oligonucleotide probe that selectively binds the specific methylated locus in the target DNA gene B3GAT1 at locus cg07845566; or wherein at step d) the platform further comprises additional oligonucleotide probes that selectively bind the specific methylated locus in the target DNA gene DYNLRB2 at locus cg00720137.

5. The method of claim 1, wherein at step c) the platform further comprises an additional oligonucleotide probe that selectively binds the specific methylated locus in the target DNA gene CDCA7 at locus cg08690031; or wherein at step d) the platform further comprises additional oligonucleotide probes that selectively bind the specific methylated locus in the target DNA gene HSD17B4 at locus cg14874121.

6. The method of claim 1, wherein at step c) the platform further comprises an additional oligonucleotide probe that selectively binds the specific methylated locus in the target DNA gene ETS1 at locus cg14998713; or wherein at step d) the platform further comprises additional oligonucleotide probes that selectively bind the specific methylated locus in the target DNA gene HSD17B8 at locus cg07433344.

7. The method of claim 1, wherein at step c) the platform further comprises an additional oligonucleotide probe that selectively binds the specific methylated locus in the target DNA gene EVI1 at locus cg14228238; or wherein at step d) the platform further comprises additional oligonucleotide probes that selectively bind the specific methylated locus in the target DNA gene IRF7 at locus cg16541031.

8. The method of claim 1, wherein at step c) the platform further comprises an additional oligonucleotide probe that selectively binds the specific methylated locus in the target DNA gene FAM78A at locus cg12998491; or wherein at step d) the platform further comprises additional oligonucleotide probes that selectively bind the specific methylated locus in the target DNA gene PER1 at locus cg01980637.

9. The method of claim 1, wherein at step c) the platform further comprises an additional oligonucleotide probe that selectively binds the specific methylated locus in the target DNA gene FAM89A at locus cg00679738; or wherein at step d) the platform further comprises additional oligonucleotide probes that selectively bind the specific methylated locus in the target DNA gene PISD at locus cg01980637.

10. The method of claim 1, wherein at step c) the platform further comprises an additional oligonucleotide probe that selectively binds the specific methylated locus in the target DNA gene FLJ31951 at locus cg01657408; or wherein at step d) the platform further comprises additional oligonucleotide probes that selectively bind the specific methylated locus in the target DNA gene WNK4 at locus cg08108311.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial
<220> FEATURE:
<223> OTHER INFORMATION: QM-MSP Primer

<400> SEQUENCE: 1
gygtaattaa ttagaaggtt tttt                                          24

<210> SEQ ID NO 2
<211> LENGTH: 20
<212> TYPE: DNA
<213> ORGANISM: Artificial
<220> FEATURE:
<223> OTHER INFORMATION: QM-MSP Primer

<400> SEQUENCE: 2
aacacctacc ttccaaatac                                               20

<210> SEQ ID NO 3
<211> LENGTH: 21
<212> TYPE: DNA
<213> ORGANISM: Artificial
<220> FEATURE:
<223> OTHER INFORMATION: QM-MSP Primer

<400> SEQUENCE: 3
gcgcgttaat cgtaggcgtt t                                             21

```
<210> SEQ ID NO 4
<211> LENGTH: 22
<212> TYPE: DNA
<213> ORGANISM: Artificial
<220> FEATURE:
<223> OTHER INFORMATION: QM-MSP Primer

<400> SEQUENCE: 4
cccaatacga tacgacctta ac                                              22

<210> SEQ ID NO 5
<211> LENGTH: 24
<212> TYPE: DNA
<213> ORGANISM: Artificial
<220> FEATURE:
<223> OTHER INFORMATION: QM-MSP Primer

<400> SEQUENCE: 5
tggtgtgtta attgtaggtg tttt                                            24

<210> SEQ ID NO 6
<211> LENGTH: 23
<212> TYPE: DNA
<213> ORGANISM: Artificial
<220> FEATURE:
<223> OTHER INFORMATION: QM-MSP Primer

<400> SEQUENCE: 6
cccaatacaa tacaacctta acc                                             23

<210> SEQ ID NO 7
<211> LENGTH: 28
<212> TYPE: DNA
<213> ORGANISM: Artificial
<220> FEATURE:
<223> OTHER INFORMATION: Labled probe

<400> SEQUENCE: 7
cgtacctttt aataacccgt aaaatcga                                        28

<210> SEQ ID NO 8
<211> LENGTH: 30
<212> TYPE: DNA
<213> ORGANISM: Artificial
<220> FEATURE:
<223> OTHER INFORMATION: Labled Probe

<400> SEQUENCE: 8 acatacctttt aaataaccca taaaatcaac                                     30
```